United States Patent [19]
Mackey et al.

[11] Patent Number: 6,121,165
[45] Date of Patent: *Sep. 19, 2000

[54] WET-LIKE CLEANING ARTICLES

[75] Inventors: Larry Neil Mackey, Fairfield; Gregory Charles Gordon; Nancy Kim Enright, both of Cincinnati, all of Ohio

[73] Assignee: The Procter & Gamble Company, Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 09/121,504

[22] Filed: Jul. 23, 1998

Related U.S. Application Data

[60] Provisional application No. 60/054,389, Jul. 31, 1997.

[51] Int. Cl.$^7$ .......................... B32B 27/04; B32B 27/12; B32B 5/02
[52] U.S. Cl. .................. 442/84; 442/64; 442/71; 442/79; 442/81; 442/82; 106/271; 106/285; 162/135; 162/136; 162/137; 252/310; 252/311; 514/938
[58] Field of Search .................. 442/64, 71, 79, 442/81, 82, 84; 514/938; 106/271, 285; 162/135, 136, 137; 252/310, 311

[56] References Cited

U.S. PATENT DOCUMENTS

| | | | |
|---|---|---|---|
| 2,868,824 | 1/1959 | Haluska | 260/448.2 |
| 3,215,707 | 11/1965 | Rense | 260/326.3 |
| 3,231,587 | 1/1966 | Rense | 260/346.8 |
| 3,818,533 | 6/1974 | Scheuer | 15/104.93 |
| 3,819,530 | 6/1974 | Ratledge et al. | 252/311.5 |
| 3,847,637 | 11/1974 | Luszczak | 106/271 |
| 3,896,807 | 7/1975 | Buchalter | 128/261 |
| 3,919,149 | 11/1975 | Cushman et al. | 260/28.5 AV |
| 3,965,518 | 6/1976 | Muoio | 15/104.93 |
| 3,982,993 | 9/1976 | Fife | 162/158 |
| 4,043,829 | 8/1977 | Ratledge et al. | 106/271 |
| 4,082,887 | 4/1978 | Coates | 428/289 |
| 4,104,403 | 8/1978 | Barker et al. | 424/365 |
| 4,112,167 | 9/1978 | Dake et al. | 428/154 |
| 4,117,199 | 9/1978 | Gotoh et al. | 428/486 |
| 4,122,029 | 10/1978 | Gee et al. | 252/309 |
| 4,137,358 | 1/1979 | Hartz | 428/272 |
| 4,203,877 | 5/1980 | Baker | 260/18 |

(List continued on next page.)

FOREIGN PATENT DOCUMENTS

| | | | |
|---|---|---|---|
| 1 132 908 | 10/1982 | Canada | 167/310 |
| 0 110 678 A2 | 6/1984 | European Pat. Off. | C08K 7/00 |
| 0 259 034 A2 | 3/1988 | European Pat. Off. | A61K 7/00 |
| 0 365 160 B1 | 4/1990 | European Pat. Off. | A61K 7/40 |
| 0 501 791 A3 | 9/1992 | European Pat. Off. | C08G 77/46 |

(List continued on next page.)

*Primary Examiner*—Blaine Copenheaver
*Assistant Examiner*—Arti Singh
*Attorney, Agent, or Firm*—Donald E. Hasse; Caroline Wei-Berk; Carl J. Roof

[57] ABSTRACT

Disclosed are articles useful in cleansing, and particularly wet-like cleansing wipes and toilet tissue. These articles are essentially dry to the touch prior to use, but deliver liquid when subjected to in-use shear and compressive forces. In one aspect, the articles of the present invention comprise a carrier and an emulsion applied to the carrier, the emulsion comprising a continuous external nonpolar phase and an internal polar phase dispersed in the external nonpolar phase, wherein the article is capable of retaining fluid prior to use. In another aspect, the emulsion-treated articles exhibit improved ability to release fluid when subjected to in-use pressures. The articles of the present invention offer a number of significant advantages over prior cleaning products when in the form of wet-like cleansing wipes such as those used for cleaning of hardsurfaces (e.g., floors, countertops, sinks, bathtubs, toilets, and the like) and wet-like toilet tissue. The articles can in general be used in any applications requiring the delivery of polar materials, in particular water and water-soluble or dispersible actives.

36 Claims, 5 Drawing Sheets

U.S. PATENT DOCUMENTS

| | | | |
|---|---|---|---|
| 4,246,423 | 1/1981 | Martin | 556/423 |
| 4,293,611 | 10/1981 | Martin | 428/266 |
| 4,339,276 | 7/1982 | Yokoyama et al. | 106/271 |
| 4,377,649 | 3/1983 | Sweeney et al. | 524/49 |
| 4,381,241 | 4/1983 | Romenesko et al. | 252/8.5 P |
| 4,385,049 | 5/1983 | Cuca | 424/167 |
| 4,421,656 | 12/1983 | Donatelli et al. | 252/8.5 P |
| 4,446,051 | 5/1984 | Berthod et al. | 252/309 |
| 4,468,254 | 8/1984 | Yokoyama et al. | 106/271 |
| 4,481,243 | 11/1984 | Allen | 428/154 |
| 4,513,051 | 4/1985 | Lavash | 428/212 |
| 4,514,345 | 4/1985 | Johnson et al. | 264/22 |
| 4,520,160 | 5/1985 | Brown | 524/765 |
| 4,606,913 | 8/1986 | Aronson et al. | 424/59 |
| 4,698,178 | 10/1987 | Hüttinger et al. | 252/309 |
| 4,708,753 | 11/1987 | Forsberg | 149/2 |
| 4,782,095 | 11/1988 | Gum | 514/937 |
| 4,801,447 | 1/1989 | Gum | 424/68 |
| 4,844,756 | 7/1989 | Forsberg | 149/2 |
| 4,853,474 | 8/1989 | Bahr et al. | 556/445 |
| 4,875,927 | 10/1989 | Tadros | 71/94 |
| 4,948,531 | 8/1990 | Fuggini et al. | |
| 4,986,882 | 1/1991 | Mackey et al. | 162/109 |
| 5,021,405 | 6/1991 | Klimisch | 514/63 |
| 5,047,175 | 9/1991 | Forsberg | 252/356 |
| 5,133,972 | 7/1992 | Ferrini et al. | 424/449 |
| 5,136,068 | 8/1992 | Bahr et al. | 556/445 |
| 5,162,378 | 11/1992 | Guthauser | 514/785 |
| 5,210,102 | 5/1993 | Klimisch | 514/784 |
| 5,245,025 | 9/1993 | Trokhan et al. | 536/56 |
| 5,247,044 | 9/1993 | Crivello et al. | 528/15 |
| 5,277,761 | 1/1994 | Van Phan et al. | 162/109 |
| 5,292,503 | 3/1994 | Raleigh et al. | 424/59 |
| 5,354,425 | 10/1994 | Mackey et al. | 162/135 |
| 5,362,482 | 11/1994 | Yoneyama et al. | 424/69 |
| 5,378,455 | 1/1995 | Kealey et al. | 424/73 |
| 5,387,417 | 2/1995 | Rentsch | 424/401 |
| 5,470,551 | 11/1995 | Dubief et al. | 424/70.12 |
| 5,482,703 | 1/1996 | Pings | 424/70.12 |
| 5,503,715 | 4/1996 | Trokhan et al. | 162/296 |
| 5,525,345 | 6/1996 | Warner et al. | 424/402 |
| 5,534,326 | 7/1996 | Trokhan et al. | 428/131 |
| 5,607,414 | 3/1997 | Richards et al. | 604/378 |
| 5,624,676 | 4/1997 | Mackey et al. | 424/414 |
| 5,763,332 | 6/1998 | Gordon et al. | 442/84 |

FOREIGN PATENT DOCUMENTS

| | | | |
|---|---|---|---|
| 0 545 002 A1 | 6/1993 | European Pat. Off. | C08G 77/46 |
| 0 631 774 A1 | 1/1995 | European Pat. Off. | A61K 9/113 |
| 2 321 389 | 12/1976 | France | B32B 29/02 |
| 3341770 A1 | 5/1983 | Germany | A61K 9/06 |
| 155758 | 9/1981 | India | A61K 7/00 |
| 2/1522920 | 6/1990 | Japan | A61K 7/50 |
| 3/168118 | 7/1991 | Japan | A47L 13/17 |
| 05070337 | 3/1993 | Japan | A61K 7/48 |
| 59144426 | 8/1994 | Japan . | |
| 1059541 | 2/1967 | United Kingdom . | |
| 2055689 | 3/1981 | United Kingdom | B32B 3/30 |
| 2113236 | 8/1983 | United Kingdom | C08L 83/12 |
| WO 87/03613 | 6/1987 | WIPO | C10M 173/00 |
| WO 94/02120 | 2/1994 | WIPO | A61K 9/113 |
| WO 95/16824 | 6/1995 | WIPO | D21H 17/14 |
| WO 96/14835 | 5/1996 | WIPO | A61K 9/70 |
| WO 96/34035 | 10/1996 | WIPO | C08J 3/03 |
| WO 97/40814 | 11/1997 | WIPO | A61K 7/50 |
| WO/97/40815 | 11/1997 | WIPO | A61K 7/50 |
| WO 98/24871 | 6/1998 | WIPO | C11D 7/44 |

WET-LIKE CLEANING ARTICLES

CROSS REFERENCE TO RELATED APPLICATION

This application claims the benefit of U.S. Provisional Application No. 60/054,389, filed Jul. 31, 1997.

TECHNICAL FIELD

This application relates to articles that are useful as wet-like cleaning wipes. The application particularly relates to wet-like cleaning articles which are capable of delivering significant levels of liquid upon use, but which are essentially dry to the touch prior to use. The articles are useful for any application where liquid is desired during the cleaning operation. In particular, the articles of the present invention are useful as hard surface cleaning wipes, toilet tissue, personal cleaning wipes such as baby wipes and the like.

BACKGROUND OF THE INVENTION

Nonwoven webs or sheets such as those made of paper find extensive use in modern society in the context of household cleaning activity. Paper towels, for example, are a staple item of commerce which have long been used to wipe up liquid spills and to remove stains and/or soil from hard surfaces such as window glass, countertops, sinks, porcelain and metal fixtures, walls and the like, and from other surfaces such as carpeting or furniture. Similarly, nonwoven sheets have been employed extensively in the context of wipes for personal cleaning, such as toilet and facial tissue.

Paper towels products which are especially useful for household cleaning have attributes which include relatively low density, high bulk, acceptable softness, high absorbency for both aqueous and nonaqueous liquids and acceptable strength and integrity, especially when wet. Prior art towel products having such attributes, and processes for their preparation, have been disclosed, for example, U.S. Pat. No. 3,905,863, issued Sep. 16, 1975 to Ayers; U.S. Pat. No. 3,974,025, issued Aug. 10, 1976 to Ayers; U.S. Pat. No. 4,191,609, issued Mar. 4, 1980 to Trokhan; U.S. Pat. No. 4,440,597, issued Apr. 3, 1984 to Wells and Hensler; U.S. Pat. No. 4,529,840, issued Jul. 16, 1985 to Trokhan; and U.S. Pat. No. 4,637,859, issued Jan. 20, 1987 to Trokhan. Paper towels, such as those of the types described in the foregoing patents, are especially useful for absorbing and wiping up liquid spills from both hard surfaces and other surfaces such as furniture and carpets. Paper towel products, however, are also frequently used, generally in combination with liquid cleaning solutions or solvents, to remove soil or stains from surfaces to which such soil or stains may be especially securely affixed. Such soil or stains, for example, may include food material on stove, oven, or cooking utensil surfaces, soap scum found in bathtubs and sinks, food and beverage stains on kitchen counters, ink or crayon markings on walls and furniture, and the like. These prior art materials typically require the consumer to clean soils and stains using a separate cleaning solution and wiping article, which involves a level of inconvenience.

Paper products used as toilet tissue for anal cleaning are also essentially dry, low density tissue papers that rely exclusively on mechanical processes to remove fecal matter from the perianal skin. These conventional products are rubbed against the perianal skin, typically with a pressure of about 1 psi (7 kilopascals) and basically scrape or abrade the fecal matter from the skin. After the first few wipes, the upper portion of the soil layer is removed because the wiping process is able to overcome the soil—soil cohesive forces that exist within the fecal matter. A cleavage is thereby created in the soil layer itself with the upper portion of the fecal layer being removed and the lower portion of the soil remaining adhered to the perianal skin. Conventional toilet tissue products are absorbent and with each successive wipe the fecal matter becomes increasingly dehydrated, causing it to adhere more tenaciously to the perianal skin and hair and making its removal difficult in the extreme. Pressing the tissue forcefully against the perianal skin will remove more of the fecal matter but is intensely painful for people suffering from anal disorders and can excoriate even normal perianal skin, potentially causing irritation, inflammation, pain, bleeding, and infection.

To address the issue of convenience for wiping articles, pre-wetted wiping articles have been developed, particularly in the area of baby wipes. These pre-wetted wipes are generally kept in a dispenser and are typically soaked in a reservoir of a moistening solution. There is often a lack of consistency in terms of the moisture content of each of the wipes, with those initially used having less liquid than those used later and the wipes feel cold to the touch. Also, because the main purpose of such wipes is to clean, these wipes generally exhibit relatively poor post-cleaning absorbency.

Co-pending U.S. patent application Ser. No. 08/877,735 (hereafter "'735 application"), filed Jun. 17, 1997 by L. Mackey et al., discloses and claims wet-like cleansing articles that are especially useful in removing perianal soils. These cleansing articles comprise a substrate material (e.g., a nonwoven) that is treated with a water-in-lipid emulsion. These articles have a number of significant advantages over prior leaning products, especially when in the form of wet-like cleansing articles used to remove perianal soils. These articles release significant quantities of polar liquids (e.g., water) during use for comfortable, more effective cleaning. The continuous lipid phase of the emulsion is sufficiently brittle so as to be easily disrupted by low shear contact (e.g., during the wiping of the skin) to readily release this internal polar phase, but sufficiently tough at elevated temperatures where the lipid is melted to avoid premature release of the polar phase during the rigors of processing. The continuous lipid phase of these articles is also sufficiently stable during storage so as to prevent significant evaporation of the internal polar phase. The normal tensile strength and flushability properties of these articles are not adversely affected when treated with the high internal phase inverse emulsions of the present invention. As a result, users of these articles get comfortable, efficient, moist cleaning without having to change their normal cleaning habits. The application also indicates that the technology is readily useful with other wipes, including wipes for cleaning hard surfaces.

Co-pending U.S. patent application Ser. No. 08/759,589 (hereafter "'589 application"), filed Dec. 5, 1996 by L. Mackey et al. and co-pending U.S. patent application Ser. No. 08/759,547 (hereafter "'547 application"), filed Dec. 5, 1996 by L. Mackey et al., describe wet-like cleaning wipes similar to those described in the '735 application, but which utilize emulsifier systems that provide enhanced fluid retention by the emulsion.

In spite of the significant improvements over prior cleansing articles, the articles described in the '735 application, the '589 application and the '547 application do exhibit some internal phase liquid loss over time, particularly after the articles have been stored at relatively high temperatures (e.g., 125° F.), such as are commonly encountered during shipment and storage in warehouses, trucks, etc. In addition, depending on the nature of substrate utilized, the amount of shear forces applied to the article during use may not be sufficient to release all (or even most) of the entrapped internal phase. To compensate for the level of liquid lost during storage and/or the level of liquid that remains trapped in the emulsion, substrates may necessarily be treated with relatively higher levels of emulsion. If such additional levels are needed, this may negatively impact the processing and economics of the articles.

Accordingly, it would be desirable to provide products for cleaning that offer the benefits provided by the cleansing articles described in the co-pending applications discussed above, but which more efficiently deliver liquid during the wiping process.

Accordingly, it is an object of the present invention to provide nonwoven, preferably paper-based, wiping articles which (i) are initially dry to the touch, but are capable of delivering liquid during the wiping process, (ii) exhibit minimal evaporation of the liquid portion of the article prior to use, (iii) readily and efficiently deliver liquid during the wiping process, and (iv) have sufficient wet strength integrity to withstand the rigors of the wiping process.

SUMMARY OF THE INVENTION

The present invention relates to articles useful in cleansing, and particularly wet-like cleansing wipes and toilet tissue. These articles are essentially dry to the touch prior to use, but deliver liquid when subjected to in-use shear and compressive forces.

In one aspect, the present invention relates to articles that comprise:
 a. a carrier; and
 b. an emulsion applied to the carrier, the emulsion comprising a continuous external nonpolar phase and an internal polar phase dispersed in the external nonpolar phase;
 wherein the emulsion comprises at least about 40%, by weight, internal polar phase and wherein the article, after being stored in a sealed container and maintained at a temperature of 125° F. for 6 days, has an internal polar phase loss after 28 days ($IPPL_{28}$ value) of not more than about 60%.

In another aspect, the present invention relates to articles that comprise:
 a. a carrier; and
 b. an emulsion applied to the carrier, the emulsion comprising a continuous external nonpolar phase and an internal polar phase dispersed in the external nonpolar phase;
 wherein the emulsion comprises at least about 40%, by weight, internal polar phase and wherein the article has an internal polar phase release (IPPR) value of at least about 30%.

Methods for measuring $IPPL_{28}$ and IPPR values are described in detail in the Test Methods section below. Briefly, the $IPPL_{28}$ value is measured by exposing a test article to 125° F. for 6 days in a moisture impermeable container prior to measuring the amount of fluid that is lost over a 28 day period when the test sample is exposed to controlled conditions.

With respect to prior applications directed to emulsion-containing articles, Applicants have improved significantly upon the ability of the emulsion to retain liquid during storage, and also have improved on the ability of the emulsion to relinquish that liquid during use. While each of the respective properties of liquid retention and liquid release are important, it is apparent that a combination of these two properties is particularly beneficial. As such, as described below, particularly preferred articles of the present invention will have both the liquid retention and liquid release properties discussed herein.

The articles of the present invention offer a number of significant advantages over prior cleaning products when in the form of wet-like cleansing articles such as those used for cleaning of hardsurfaces (e.g., floors, countertops, sinks, bathtubs, toilets, and the like) and those used as toilet tissue. The articles can be used in many applications requiring the delivery of polar materials, in particular water and water-soluble or dispersible actives. These include wipes for personal cleansing, such as baby wipes, as well as those for the delivery of water-soluble or dispersible antimicrobials or pharmaceutical actives.

These articles can also perform multiple functions. For example, the high internal phase inverse emulsion applied to these articles can be formulated to provide cleaning and waxing benefits at the same time when used on items such as furniture, shoes, automobiles, and the like.

DETAILED DESCRIPTION

Figure 1:
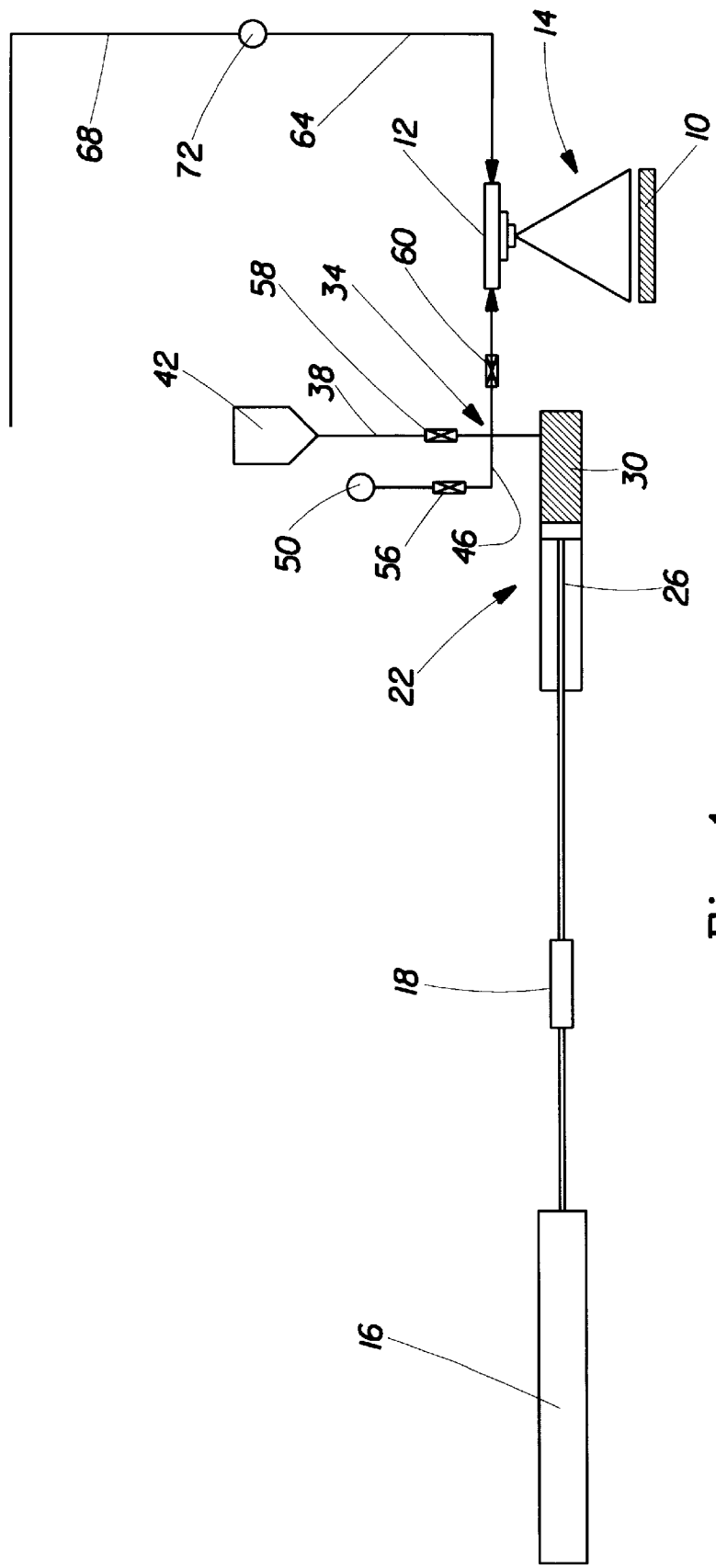
FIG. 1 is a schematic representation illustrating a spray system for applying the high internal phase inverse emulsions of the present invention to a carrier such as a treated paper web.

As used herein, the term "comprising" means that the various components, ingredients, or steps, can be conjointly employed in practicing the present invention. Accordingly, the term "comprising" encompasses the more restrictive terms "consisting essentially of" and "consisting of."

As used herein, the terms "detergent", "detersive surfactant" and "detergent surfactant" are used interchangeably, and refer to any substance that reduces the surface tension of water, specifically a surface-active agent which concentrates at oil-water interfaces, exerts emulsifying action, and thus aids in removing soils.

As used herein, the term "hydrophilic" is used to refer to surfaces that are wettable by aqueous liquids deposited thereon. Hydrophilicity and wettability are typically defined in terms of contact angle and the surface tension of the liquids and solid surfaces involved. This is discussed in detail in the American Chemical Society publication entitled *Contact Angle, Wettability and Adhesion*, edited by Robert F. Gould (Copyright 1964), which is hereby incorporated herein by reference. A surface is said to be wetted by a liquid (i.e., hydrophilic) when either the contact angle between the liquid and the surface is less than 90°, or when the liquid tends to spread spontaneously across the surface, both conditions normally co-existing. Conversely, a surface is considered to be "hydrophobic" if the contact angle is greater than 90° and the liquid does not spread spontaneously across the surface.

As used herein, the term "polar" means a molecule that possesses a dipole moment, i.e., a molecule of which the positive and negative electrical charges are permanently separated, as opposed to a "nonpolar molecule" in which the charges coincide. A "polar liquid" may comprise one or more polar constituents.

As used herein, the term "polarphilic" is used to refer to surfaces that are wettable by polar liquids deposited thereon. Polarphilicity and wettability are typically defined in terms of contact angle and the surface tension of the liquids and solid surfaces involved. A surface is said to be wetted by a polar liquid (i.e., polarphilic) when either the contact angle between the polar liquid and the surface is less than 90°, or when the polar liquid tends to spread spontaneously across the surface, both conditions normally coexisting. Conversely, a surface is considered to be "polarphobic" if the contact angle is greater than 90° and the liquid does not spread spontaneously across the surface. Since water is generally the preferred polar material used in the present invention, preferred embodiments discussed herein refer to a substrate's "hydrophilicity" and "hydrophobicity". However, use of such terms is not so limited and should be read to include "polarphilic" and "polarphobic" substrates.

All percentages, ratios and proportions used herein are by weight unless otherwise specified.

In one aspect, the present invention relates to articles that comprise:

a. a carrier; and
b. an emulsion applied to the carrier, the emulsion comprising a continuous external nonpolar phase and an internal polar phase dispersed in the external nonpolar phase;
wherein the emulsion comprises at least about 40%, by weight, internal polar phase and wherein the article, after being stored in a sealed container and maintained at a temperature of 125° F. for 6 days, has an $IPPL_{28}$ value of not more than about 60%.

In this aspect of the invention, the $IPPL_{28}$ value preferably will be not more than about 50%, more preferably not more that about 40%, still more preferably not more than about 30%, still more preferably not more than about 20% and most preferably not more than about 10%. Typically, in this aspect, the $IPPL_{28}$ value will be from about 10% to about 60%, typically from about 10% to about 50%, more typically from about 10% to about 40%. Exposure of the article to elevated temperatures (e.g., 125° F.) during storage in a container reflects the article's ability to retain liquid after the packaged article has been subjected to conditions commonly encountered during shipment and storage of the product (i.e., prior to purchase by the end user). In particular, measuring internal polar phase loss after the article is exposed to high temperatures considers the stability of the article's emulsion at such high temperatures. In those situations where the emulsion is destablized to a significant degree, excessive internal phase liquid will be released and will evaporate. Applicants have found that the ability to avoid emulsion destabilization is an important feature of the present wet-like cleaning articles. As discussed below, in measuring high temperature stability, the package containing the test sample should be subjected to 125° F. for 6 days prior to opening the package.

In another aspect, the articles of the present invention comprise:

a. a carrier; and
b. an emulsion applied to the carrier, the emulsion comprising a continuous external nonpolar phase and an internal polar phase dispersed in the external nonpolar phase;
wherein the article comprises at least about 40%, by weight, internal polar phase and wherein the article has an internal polar phase release (IPPR) value of at least about 30%.

In this aspect, the article will preferably have an IPPR value of at least about 40%, more preferably at least about 50%, more preferably at least about 60%, still more preferably at least about 70%, still more preferably at least about 80%, and most preferably at least about 90%. Typically, the articles will have an IPPR value of from about 30 to about 90%, more typically from about 40 to about 90%, still more typically from about 50 to about 90%, and still more typically from about 60 to about 90%. It is apparent that the IPPR value corresponds to the amount of liquid released from an article when the article is subjected to shear and compressive forces. In essence, the IPPR value is a measure of an article's ability to release liquid during the cleaning operation. Of course, the higher the IPPR value, the more liquid the article will deliver during use. As discussed below, the ability of an article to release fluid is largely impacted by the ability of the emulsion to release fluid when exposed to pressures during use.

While the properties of liquid retention and liquid release are independently important to articles which are initially dry but release liquid during the wiping process, in a particularly preferred embodiment, both characteristics will exist in a single article. This is particularly true in those articles wherein neither external surface of the article's carrier is coated with emulsion, such that shear forces are relatively small.

A. Carriers for High Internal Phase Inverse Emulsion

Carriers useful in the present invention can be in a variety of substrate forms. Suitable carrier substrates include woven materials, nonwoven materials, foams, sponges, battings, balls, puffs, films, and the like. Particularly preferred substrates for use in the present invention are nonwoven types. These nonwoven substrates can comprise any conventionally fashioned nonwoven sheet or web having suitable basis weight, caliper (thickness), absorbency and strength characteristics. Nonwoven substrates can be generally defined as bonded fibrous or filamentous products having a web structure, in which the fibers or filaments are distributed randomly as in "air-laying" or certain "wet-laying" processes, or with a degree of orientation, as in certain "wet-laying" or "carding" processes. The fibers or filaments of such nonwoven substrates can be natural (e.g., wood pulp, wool, silk, jute, hemp, cotton, linen, sisal or ramie) or synthetic (e.g., rayon, cellulose ester, polyvinyl derivatives, polyolefins, polyamides or polyesters) and can be bonded together with a polymeric binder resin. Examples of suitable commercially available nonwoven substrates include those marketed under the tradename Sontara® by DuPont and Polyweb® by James River Corp.

For reasons of cost, ease of manufacture and article disposability, the preferred type of nonwoven substrate used in articles of the present invention comprise those made from wood pulp fibers, i.e., paper webs. As noted, paper webs can be prepared by either air-laying or wet-laying techniques. Air-laid paper webs such as Air Tex® SC130 are commercially available from James River Corp. More conventionally, paper webs are made by wet-laying procedures. In such procedures, a web is made by forming an aqueous papermaking furnish, depositing this furnish onto a foraminous surface, such as a Fourdrinier wire, and by then removing water from the furnish, for example by gravity, by vacuum assisted drying and/or by evaporation, with or without pressing, to thereby form a paper web of desired fiber consistency. In many cases, the papermaking apparatus is set up to rearrange the fibers in the slurry of papermaking furnish as dewatering proceeds in order to form paper substrates of especially desirable strength, hand, bulk, appearance, absorbency, etc.

The papermaking furnish utilized to form the preferred paper web substrates for articles of the present invention essentially comprises an aqueous slurry of papermaking fibers (i.e., paper pulp) and can optionally contain a wide variety of chemicals such as wet strength resins, surfactants, pH control agents, softness additives, debonding agents and the like. Wood pulp in all its variations can be used to form the papermaking furnish. Wood pulps useful herein include both sulfite and sulfate pulps, as well as mechanical, thermo-mechanical and chemi-thermo-mechanical pulps, all of which are well known to those skilled in the papermaking art. Pulps derived from both deciduous or coniferous trees can be used. Preferably the papermaking furnish used to form the preferred paper web substrates for articles of the present invention comprises Kraft pulp derived from northern softwoods. It will be recognized that in addition to papermaking fibers, preferred paper webs may further comprise fibers from other sources, including synthetic fibers such as, for example, polyethylene, polyethylene terephthalate (PET), polypropylene, cellulose acetate, and the like.

A number of papermaking processes have been developed which utilize a papermaking apparatus that forms paper webs having particularly useful or desirable fiber configurations. Such configurations can serve to impart such characteristics of the paper web as enhanced bulk, absorbency and strength. One such process employs an imprinting fabric in the papermaking process that serves to impart a knuckle pattern of high density and low density zones into the resulting paper web. A process of this type, and the papermaking apparatus for carrying out this process, is described in greater detail in U.S. Pat. No. 3,301,746 (Sanford et al), issued Jan. 31, 1967, which is incorporated by reference.

Another papermaking process employs a throughdrying fabric having impression knuckles raised above the plane of the fabric. These impressions create protrusions in the throughdried sheet, and provide the sheet with stretch in the cross-machine direction. A process of this type is described in European Patent Publication No. 677,612A2, published Oct. 18, 1995 by G. Wendt et al., the disclosure of which is incorporated herein by reference.

Still another papermaking process carried out with a special papermaking apparatus is one that provides a paper web having a distinct, continuous network region formed by a plurality of "domes" dispersed throughout the network region on the substrate. Such domes are formed by compressing an embryonic web as formed during the papermaking process into a foraminous deflection member having a patterned network surface formed by a plurality of discrete isolated deflection conduits in the deflection member surface. A process of this type, and apparatus for carrying out such a process, is described in greater detail in U.S. Pat. No. 4,529,480 (Trokhan), issued Jul. 16, 1985; U.S. Pat. No. 4,637,859 (Trokhan), issued Jan. 20, 1987; and U.S. Pat. No. 5,073,235 (Trokhan), issued Dec. 17, 1991, all of which are incorporated by reference. Another type of papermaking process, and apparatus to carry it out that is suitable for making layered composite paper substrates is described in U.S. Pat. No. 3,994,771 (Morgan et al), issued Nov. 30, 1976, which is incorporated by reference.

Still another papermaking process carried out with a special papermaking apparatus is one that provides a paper web having multiple basis weight regions. Such a process is described in U.S. Pat. No. 5,245,025, issued Sep. 14, 1993 to Trokhan et al., U.S. Pat. No. 5,503,715, issued Apr. 2, 1996 to Trokhan et al., and U.S. Pat. No. 5,534,326, issued Jul. 9, 1996 to Trokhan et al., the disclosure of each of which is incorporated herein by reference. See also, co-pending U.S. patent application Ser. No. 08/886,764, filed by N. Nissing et al. on Jul. 1, 1997, the disclosure of which is incorporated by reference herein. Such substrates provide a carrier having regions that are more permeable (i.e., relatively lower basis weight regions) than other regions (i.e., higher basis weight regions).

The preferred paper web substrates can form one of two or more plies that can be lamminated together. Lamination, and lamination carried out in combination with an embossing procedure to form a plurality of protuberances in the laminated product, is described in greater detail in U.S. Pat. No. 3,414,459 (Wells), issued Dec. 3, 1968, which is incorporated by reference. These paper substrates preferably have a basis weight of between about 10 $g/m^2$ and about 100 $g/m^2$, and density of about 0.6 g/cc or less. More preferably, the basis weight will be about 40 $g/m^2$ or less and the density will be about 0.3 g/cc or less. Most preferably, the density will be between about 0.04 g/cc and about 0.2 g/cc. See Column 13, lines 61–67, of U.S. Pat. No. 5,059,282 (Ampulski et al), issued Oct. 22, 1991, which describes how the density of tissue paper is measured. (Unless otherwise specified, all amounts and weights relative to the paper web substrates are on a dry weight basis.)

In addition to papermaking fibers, the papermaking furnish used to make these paper web substrates can have other components or materials added thereto which are or later become known in the art. The types of additives desirable will be dependent upon the particular end use of the tissue sheet contemplated. For example, in products such as paper towels, facial tissues, baby wipes and other similar products, high wet strength is a desirable attribute. Thus, it is often desirable to add to the papermaking furnish chemical substances known in the art as "wet strength" resins.

A general dissertation on the types of wet strength resins utilized in the paper art can be found in TAPPI monograph series No. 29, Wet Strength in Paper and Paperboard, Technical Association of the Pulp and Paper Industry (New York, 1965). The most useful wet strength resins have generally been cationic in character. For permanent wet strength generation, polyamide-epichlorohydrin resins are cationic wet strength resins have been found to be of particular utility. Suitable types of such resins are described in U.S. Pat. No. 3,700,623 (Keim), issued Oct. 24, 1972, and U.S. Pat. No. 3,772,076 (Keim), issued Nov. 13, 1973, both of which are incorporated by reference. One commercial source of a useful polyamide-epichlorohydrin resin is Hercules, Inc. of Wilmington, Del., which markets such resins under the mark Kymene® 557H.

Polyacrylamide resins have also been found to be of utility as wet strength resins. These resins are described in U.S. Pat. Nos. 3,556,932 (Coscia et al), issued Jan. 19, 1971, and 3,556,933 (Williams et al), issued Jan. 19, 1971, both of which are incorporated by reference. One commercial source of polyacrylamide resins is American Cyanamid Co. of Stamford, Conn., which markets one such resin under the mark Parez® 631 NC.

Still other water-soluble cationic resins finding utility as wet strength resins are urea formaldehyde and melamine formaldehyde resins. The more common functional groups of these polyfunctional resins are nitrogen containing groups such as amino groups and methylol groups attached to nitrogen. Polyethylenimine type resins can also find utility in the present invention. In addition, temporary wet strength resins such as Caldas 10® (manufactured by Japan Carlit), Parez 750® (manufactured by American Cyanamide Co.), and CoBond 1000 ® (manufactured by National Starch and Chemical Company) can be used in the present invention. It is to be understood that the addition of chemical compounds such as the wet strength and temporary wet strength resins discussed above to the pulp furnish is optional and is not necessary for the practice of the present invention.

In addition to wet strength additives, it can also be desirable to include in the papermaking fibers certain dry strength and lint control additives known in the art. In this regard, starch binders have been found to be particularly suitable. In addition to reducing linting of the paper substrate, low levels of starch binders also impart a modest improvement in the dry tensile strength without imparting stiffness that could result from the addition of high levels of starch. Typically the starch binder is included in an amount such that it is retained at a level of from about 0.01 to about 2%, preferably from about 0.1 to about 1%, by weight of the paper substrate.

In general, suitable starch binders for these paper web substrates are characterized by water solubility, and hydrophilicity. Although it is not intended to limit the scope of suitable starch binders, representative starch materials include corn starch and potato starch, with waxy corn starch known industrially as amioca starch being particularly preferred. Amioca starch differs from common corn starch in that it is entirely amylopectin, whereas common corn starch contains both amylopectin and amylose. Various unique characteristics of amioca starch are further described in "Amioca—The Starch From Waxy Corn," H. H. Schopmeyer, Food Industries, December 1945, pp. 106–108 (Vol. pp. 1476–1478).

The starch binder can be in granular or dispersed form, the granular form being especially preferred. The starch binder is preferably sufficiently cooked to induce swelling of the granules. More preferably, the starch granules are swollen, as by cooking, to a point just prior to dispersion of the starch granule. Such highly swollen starch granules shall be referred to as being "fully cooked." The conditions for dispersion in general can vary depending upon the size of the starch granules, the degree of crystallinity of the granules, and the amount of amylose present. Fully cooked amioca starch, for example, can be prepared by heating an aqueous slurry of about 4% consistency of starch granules at about 190° F. (about 88° C.) for between about 30 and about 40 minutes. Other exemplary starch binders that can be used include modified cationic starches such as those modified to have nitrogen containing groups, including amino groups and methylol groups attached to nitrogen, available from National Starch and Chemical Company, (Bridgewater, N.J.), that have previously been used as pulp furnish additives to increase wet and/or dry strength.

Many of the materials described as useful as the optional hydrophilic substrate layer are inherently hydrophilic. Materials which are not naturally hydrophilic can be treated with any of a variety of hydrophilizing agents well known in the art. Suitable surfactants for hydrophilizing include, for example, ethoxylated esters such as Pegosperse® 200-ML, manufactured by Glyco Chemical, Inc. of Greenwich, Conn. ATMER® 645, manufactured by ICI, glucose amides, triblock copolymers of ethylene oxide and propylene oxide such as Pluronic® P103, manufactured by BASF, and copolymers of silicone and ethylene glycol such as DC190, manufactured by Dow Corning of Midland, Mich. Surfactants may be applied to the surface of the substrate by spraying, printing, or other suitable methods such as disclosed in U.S. Pat. No. 4,950,264, issued to Osborn on Aug. 21, 1990, the disclosure of which is incorporated herein by reference.

B. High Internal Phase Inverse Emulsion

The articles of the present invention comprise a carrier that is treated with a high internal phase inverse emulsion. The emulsion comprises: (1) a continuous nonpolar phase; (2) an emulsifier; and (3) an internal polar phase dispersed in the external nonpolar phase. This emulsion ruptures when subjected to low shear or compressive forces during use, so as to release the internal polar phase.

1. Continuous Nonpolar Phase

The continuous nonpolar external phase provides the essential stabilizing structure for the high internal phase inverse emulsions of the present invention. In particular, this continuous nonpolar phase is what keeps the dispersed internal polar phase from being prematurely released prior to use of the article, such as during shipment and storage.

The continuous nonpolar phase will preferably comprise from about 2 to about 60% of the emulsion of the present invention. Preferably, this continuous nonpolar phase will comprise a lipid and will comprise from about 3 to about 30% of the emulsion. Most preferably, this nonpolar phase will comprise from about 4 to about 15% of the emulsion.

Where the continuous external nonpolar phase is lipid-based, the major constituent is a waxy lipid material or mixture of such materials. This waxy lipid material is characterized by a peak melting point of about 30° C. or higher, as measured by Differential Scanning Calorimetry (DSC), i.e., is solid at ambient temperatures. Preferably, the lipid material has a peak melting point of about 50° C. or higher. Typically, the lipid material has a peak melting point in the range of from about 40° to about 80° C., more typically in the range of from about 50° to about 70° C.

In a preferred aspect of the present invention, the external nonpolar phase comprises at least two lipids, wherein the lipids have different melt characteristics. In particular, one lipid material will have a peak melting point in the range of from about 30 to about 60° C., preferably about 50 to about 60° C., and another lipid material will have a peak melting point in the range of from about 50 to about 90° C., preferably from about 65 to about 85° C., wherein the difference in melting point between at least two of the lipid materials is at least about 10° C., preferably at least about 15° C., still more preferably at least about 20° C. With a mixture of waxy lipid materials, a minimum of 50% of the integrated area of the DSC peak(s) will preferably be distributed at or above about 50° C. That is, at least about 50% of the waxy lipid material melts above 50° C. Applicants have found that inclusion of lipid materials having different melting points provides emulsions that are more stable after exposure to high temperatures (e.g., 125° F.) after manufacture. While not wishing to be bound by theory, it is believed that during the cooling of the emulsion after application to the carrier (or after exposure to high temperatures after article manufacture), the phase change from liquid to solid involves contraction in volume of the external nonpolar phase during which cracks or voids can form in the external phase. These cracks or voids provide an avenue for premature polar phase release (e.g., via evaporation) from the emulsion. It is believed that the lower or intermediate melting lipid in the mixture will remain fluid at the solidification point of the higher melting material, and is therefore capable of migrating to fill the cracks or voids formed by the higher melting wax as it solidifies.

In another preferred aspect, the external polar phase will comprise a significant proportion of a wax having a ASTM D-1321 penetration number at room temperature of not more than about 20¹/₁₀ mm, preferably not more than about 15¹/₁₀ mm, still more preferably not more than about 10¹/₁₀ mm. ASTM D-1321 numbers are descriptive of the hardness of the material being measured. In this regard, "harder" (i.e., more brittle) waxes fracture more readily than "softer" waxes, which tend to deform without rupture under pressures commonly encountered during wiping. Thus, external polar phase materials having the above penetration numbers enable the emulsion to more readily break and release internal polar phase during the normal cleaning operation.

Although the external phase is solid at ambient temperatures, it also needs to be fluid or plastic at those temperatures at which the high internal phase inverse emulsion is applied to the carrier. Moreover, even though the external phase material(s) is fluid or plastic at those temperatures at which the emulsion is applied to the carrier substrate, it should still desirably be somewhat stable (i.e., minimal coalescence of emulsion micro-droplets) for extended periods of time at elevated temperatures (e.g., about 50° C. or higher) that are normally encountered during storage and distribution of the articles of the present invention. This material also needs to be sufficiently brittle at the shear conditions of use of the article such that it ruptures and releases the dispersed internal polar phase. These materials should also desirably provide a good feel to the skin when used in personal care products such as wet-like cleansing wipes and tissue used in perianal cleaning.

Suitable preferred waxy lipid materials for use in the high internal phase inverse emulsion of the present invention include natural and synthetic waxes, as well as other oil soluble materials having a waxy consistency. As used herein, the term "waxes" refers to organic mixtures or compounds that are generally water-insoluble and tend to exist as amorphous or microcrystalline or crystalline solids at ambient temperatures (e.g., at about 25° C.). Suitable waxes include various types of hydrocarbons, as well as esters of certain fatty acids and fatty alcohols. They can be derived from natural sources (i.e., animal, vegetable or mineral) or they can be synthesized. As discussed above, mixtures of these various waxes can also be used, and are preferred in certain embodiments.

Some representative animal and vegetable waxes that can be used in the present invention include beeswax, carnauba, spermaceti, lanolin, shellac wax, candelilla, and the like. Particularly preferred animal and vegetable waxes are beeswax, lanolin and candelilla. Representative waxes from mineral sources that can be used in the present invention include petroleum-based waxes such as paraffin, petrolatum and microcrystalline wax, and fossil or earth waxes such as white ceresine wax, yellow ceresine wax, white ozokerite wax, and the like. Particularly preferred mineral waxes are petrolatum, microcrystalline wax, yellow ceresine wax, and white ozokerite wax. Representative synthetic waxes that can be used in the present invention include ethylenic polymers such as polyethylene wax, chlorinated naphthalenes such as "Halowax," hydrocarbon type waxes made by Fischer-Tropsch synthesis, and the like. Particularly preferred synthetic waxes are polyethylene waxes, particularly the branched polyethylene waxes such as Affinity SM 8400 from Dow Chemical Company.

Besides the waxy lipid material, the continuous lipid phase can include minor amounts of other lipophilic or lipid-miscible materials. These other lipophilic/lipid miscible materials are typically included for the purpose of stabilizing the emulsion to minimize loss of the internal polar phase or for improving the aesthetic feel of the emulsion on the skin. Suitable materials of this type that can be present in the continuous lipid phase include hot melt adhesives such as Findley 193-336 resin, long chain alcohols such as cetyl alcohol, stearyl alcohol, and cetaryl alcohol, water-insoluble soaps such as aluminum stearate, silicone polymers such as polydimethylsiloxanes, hydrophobically modified silicone polymers such as phenyl trimethicone, and the like. Other suitable lipophilic/lipid miscible materials include polyol polyesters. By "polyol polyester" is meant a polyol having at least 4 ester groups. By "polyol" is meant a polyhydric alcohol containing at least 4, preferably from 4 to 12, and, most preferably from 6 to 8, hydroxyl groups. Polyols include monosaccharides, disaccharides and trisaccharides, sugar alcohols and other sugar derivatives (e.g., alkyl glycosides), polyglycerols (e.g., diglycerol and triglycerol), pentaerythritol, and polyvinyl alcohols. Preferred polyols include xylose, arabinose, ribose, xylitol, erythritol, glucose, methyl glucoside, mannose, galactose, fructose, sorbitol, maltose, lactose, sucrose, raffinose, and maltotriose. Sucrose is an especially preferred polyol. With respect to the polyol polyesters useful herein, it is not necessary that all of the hydroxyl groups of the polyol be esterified, however disaccharide polyesters should have no more than 3, and more preferably no more than 2 unesterified hydroxyl groups. Typically, substantially all (e.g., at least about 85%) of the hydroxyl groups of the polyol are esterified. In the case of sucrose polyesters, typically from about 7 to 8 of the hydroxyl groups of the polyol are esterified.

By "liquid polyol polyester" is meant a polyol polyester from the hereinbefore described groups having a fluid consistency at or below about 37° C. By "solid polyol polyester" is meant a polyol polyester from the hereinbefore described groups having a plastic or solid consistency at or above about 37° C. Liquid polyol polyesters and solid polyol polyesters may be successfully employed as emollients and immobilizing agents, respectively, in emulsions of the present invention. In some cases, solid polyol polyesters may also provide some emolliency functionality.

Applicants have discovered that in one respect, the composition of the external nonpolar phase directly impacts the ability of the emulsion to retain fluid after the product has been stored at elevated temperatures (e.g., 125° F.). In another respect, the hardness properties of the external phase also impacts the emulsion's ability to break and release liquid in use. Separately, the emulsifier(s) used in making the emulsion appears to directly impact the ability of the emulsion to break and release internal polar phase during typical in-use shear and compressive forces. (Preferred emulsifier properties for achieving these benefits are discussed in detail below.) Thus, by combining preferred properties of the external nonpolar phase and the emulsifier, the emulsion of the present articles can be tailored to provide desired fluid retention and fluid release characteristics.

2. Internal Polar Phase

Typically, the major component of the high internal phase inverse emulsions of the present invention is the dispersed internal polar phase. In preferred embodiments, the polar phase will contain a significant percentage of water, preferably at least about 60%, by weight of the emulsion, more preferably at least about 75%, by weight, still more preferably at least about 90%, by weight.

The internal polar phase can provide a number of different benefits when released. For example, in wet-like cleaning articles for perianal cleaning where the internal polar phase is water, it is this released water that provides the primary cleansing action for these articles.

In one embodiment where the article of the present invention will be used as a hardsurface wipe, the internal polar phase (preferably comprising water as a major constituent) may be a disinfecting polar phase comprising an antimicrobial compound, preferably an essential oil or an active thereof, and a bleach, preferably a peroxygen bleach. Disinfecting wipes comprising such an internal disinfecting polar phase provide effective disinfecting performance on a surface while being safe to the surface treated.

By "effective disinfecting performance" it is meant herein that the disinfecting wipes of the present invention allow significant reduction in the amount of bacteria on an infected surface. Indeed, effective disinfection may be obtained on various microorganisms including Gram positive bacteria like *Staphylococcus aureus*, and Gram negative bacteria like *Pseudomonas aeruginosa*, as well as on more resistant micro-organisms like fungi (e.g., *Candida albicans*) present on infected surfaces.

Another advantage of the disinfecting wipes according to the present invention is that besides the disinfection properties delivered, good cleaning is also provided as the disinfecting polar phase may further comprise surfactants and/or solvents.

An essential element of the internal disinfecting polar phase is an antimicrobial compound typically selected from the group consisting of an essential oil and an active thereof, paraben (e.g., methyl paraben, ethyl paraben), glutaraldehyde and mixtures thereof. Essential oils or actives thereof are the preferred antimicrobial compounds to be used herein.

Suitable essential oils or actives thereof to be used herein are those essential oils which exhibit antimicrobial activity and more particularly antibacterial activity. By "actives of essential oils" it is meant herein any ingredient of essential oils that exhibits antimicrobial/antibacterial activity. A further advantage of said essential oils and actives hereof is that they impart pleasant odor to the disinfecting wipes according to the present invention without the need of adding a perfume. Indeed, the disinfecting wipes according to the present invention deliver not only excellent disinfecting performance on infected surfaces but also good scent.

Such essential oils include, but are not limited to, those obtained from thyme, lemongrass, citrus, lemons, oranges, anise, clove, aniseed, cinnamon, geranium, roses, mint, lavender, citronella, eucalyptus, peppermint, camphor, sandalwood and cedar and mixtures thereof. Actives of essential oils to be used herein include, but are not limited to, thymol (present for example in thyme), eugenol (present for example in cinnamon and clove), menthol (present for example in mint), geraniol (present for example in geranium and rose), verbenone (present for example in vervain), eucalyptol and pinocarvone (present in eucalyptus), cedrol (present for example in cedar), anethol (present for example in anise), carvacrol, hinokitiol, berberine, terpineol, limonene, methyl salycilate and mixtures thereof. Preferred actives of essential oils to be used herein are thymol, eugenol, verbenone, eucalyptol, carvacrol, limonene and/or geraniol. Thymol may be commercially available for example from Aldrich, eugenol may be commercially available for example from Sigma, Systems—Bioindustries (SBI)—Manheimer Inc.

Typically, the antimicrobial compound or mixtures thereof will be present in the internal polar phase at a level of from 0.001% to 5%, preferably from 0.001% to 3%, more preferably from 0.005% to 1%, by weight of total internal polar phase.

An important element of the internal disinfecting polar phase is a bleach or mixtures thereof. Any bleach known to those skilled in the art may be suitable to be used herein including any chlorine bleach as well as any peroxygen bleach. The presence of the bleach, preferably the peroxygen bleach, in the disinfecting wipes of the present invention contribute to the disinfection properties of the wipes.

Suitable chlorine bleaches to be used herein include any compound capable of releasing chlorine when said compound is in contact with water. Suitable chlorine bleaches include alkali metal dichloroisocyanurates as well as alkali metal hypohalites like hypochlorite and/or hypobromite. Preferred chlorine bleaches are alkali metal hypochlorites. Various forms of alkali metal hypochlorite are commercially available, for instance sodium hypochlorite.

Preferred bleaches for use herein are peroxygen bleaches, more particularly hydrogen peroxide, or a water soluble source thereof, or mixtures thereof. Hydrogen peroxide is particularly preferred.

Peroxygen bleaches like hydrogen peroxide are preferred herein as they are generally well accepted from an environmental point of view. For example the decomposition products of hydrogen peroxide are oxygen and water.

As used herein, a hydrogen peroxide source refers to any compound which produces perhydroxyl ions when said compound is in contact with water. Suitable water-soluble sources of hydrogen peroxide for use herein include percarbonates, persilicates, persulphates such as monopersulfate, perborates, peroxyacids such as diperoxydodecandioic acid (DPDA), magnesium perphthalic acid, dialkylperoxides, diacylperoxides, performed percarboxylic acids, organic and inorganic peroxides and/or hydroperoxides and mixtures thereof.

Typically, the bleach or mixtures thereof is present at a level of from 0.001% to 15% by weight of the total internal polar phase, preferably from 0.001% to 5%, and more preferably from 0.005% to 2%.

The internal disinfecting polar phase may further comprise a detersive surfactant or a mixture thereof. Typically, the surfactant or mixtures thereof is present at a level of from 0.001% to 40% by weight of the total internal polar phase, preferably from 0.01% to 10% and more preferably from 0.05% to 2%.

Suitable detersive surfactants to be used in the present invention include any surfactant known to those skilled in the art like nonionic, anionic, cationic, amphoteric and/or zwitterionic surfactants. Preferred detersive surfactants to be used herein are the amphoteric and/or zwitterionic surfactants.

Suitable amphoteric detersive surfactants to be used herein include amine oxides of the formula $R^1R^2R^3NO$, wherein each of $R^1$, $R^2$ and $R^3$ is independently a saturated, substituted or unsubstituted, linear or branched hydrocarbon chain having from 1 to 30 carbon atoms. Preferred amine oxide surfactants to be used according to the present invention are amine oxides of the formula $R^1R^2R^3NO$, wherein $R^1$ is an hydrocarbon chain having from 1 to 30 carbon atoms, preferably from 6 to 20, more preferably from 8 to 16, most preferably from 8 to 12, and wherein $R^2$ and $R^3$ are independently substituted or unsubstituted, linear or branched hydrocarbon chains having from 1 to 4 carbon atoms, preferably from 1 to 3 carbon atoms, and more preferably are methyl groups. $R^1$ may be a saturated, substituted or unsubstituted, linear or branched hydrocarbon chain. Suitable amine oxides for use herein are for instance natural blend $C_8$–$C_{10}$ amine oxides as well as $C_{12}$–$C_{16}$ amine oxides commercially available from Hoechst. Amine oxides are preferred herein as they deliver effective cleaning performance and further participate to the disinfecting properties of the disinfecting wipes herein.

Suitable zwitterionic surfactants to be used herein contain both cationic and anionic hydrophilic groups on the same molecule at a relatively wide range of pH's. The typical cationic group is a quaternary ammonium group, although other positively charged groups like phosphonium, imidazolinium and sulfonium groups can be used. The typical anionic hydrophilic groups are carboxylates and sulfonates, although other groups such as sulfates, phosphonates, and the like can be used. A generic formula for some zwitterionic surfactants to be used herein is

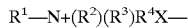

wherein $R^1$ is a hydrophobic group; $R^2$ and $R^3$ are each $C_1$–$C_4$ alkyl, hydroxy alkyl or other substituted alkyl group which can also be joined to form ring structures with the N; $R^4$ is a moiety joining the cationic nitrogen atom to the hydrophilic group and is typically an alkylene, hydroxy alkylene, or polyalkoxy group containing from 1 to 10 carbon atoms; and X is the hydrophilic group which is preferably a carboxylate or sulfonate group. Preferred hydrophobic groups $R^1$ are alkyl groups containing from 1 to 24, preferably less than 18, more preferably less than 16 carbon atoms. The hydrophobic group can contain unsaturation and/or substituents and/or linking groups such as aryl groups, amido groups, ester groups and the like. In general, the simple alkyl groups are preferred for cost and stability reasons.

Highly preferred zwitterionic surfactants include betaine and sulphobetaine surfactants, derivatives thereof or mixtures thereof. Said betaine or sulphobetaine surfactants are preferred herein as they help disinfection by increasing the permeability of the bacterial cell wall, thus allowing other active ingredients to enter the cell.

Furthermore, due to the mild action profile of said betaine or sulphobetaine surfactants, they are particularly suitable for the cleaning of delicate surfaces, e.g., hard surfaces in contact with food and/or babies. Betaine and sulphobetaine surfactants are also extremely mild to the skin and/or surfaces to be treated.

Suitable betaine and sulphobetaine surfactants to be used herein are the betaine/sulphobetaine and betaine-like detergents wherein the molecule contains both basic and acidic groups which form an inner salt giving the molecule both cationic and anionic hydrophilic groups over a broad range of pH values. Some common examples of these detergents are described in U.S. Pat. Nos. 2,082,275, 2,702,279 and 2,255,082, incorporated herein by reference. Preferred betaine and sulphobetaine surfactants herein are according to the formula

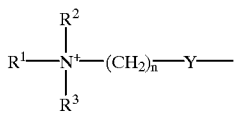

wherein $R^1$ is a hydrocarbon chain containing from 1 to 24 carbon atoms, preferably from 8 to 18, more preferably from 12 to 14, wherein $R^2$ and $R^3$ are hydrocarbon chains containing from 1 to 3 carbon atoms, preferably 1 carbon atom, wherein n is an integer from 1 to 10, preferably from 1 to 6, more preferably is 1, Y is selected from the group consisting of carboxyl and sulfonyl radicals and wherein the sum of $R^1$, $R^2$ and $R^3$ hydrocarbon chains is from 14 to 24 carbon atoms, or mixtures thereof.

Examples of particularly suitable betaine surfactants include $C_{12}$–$C_{18}$ alkyl dimethyl betaine such as coconutbetaine and $C_{10}$–$C_{16}$ alkyl dimethyl betaine such as laurylbetaine. Coconutbetaine is commercially available from Seppic under the trade name of Amonyl 265®. Laurylbetaine is commercially available from Albright & Wilson under the trade name Empigen BB/L®.

Other specific zwitterionic surfactants have the generic formulas:

wherein each $R^1$ is a hydrocarbon, e.g. an alkyl group containing from 8 up to 20, preferably up to 18, more preferably up to 16 carbon atoms, each $R^2$ is either a hydrogen (when attached to the amido nitrogen), short chain alkyl or substituted alkyl containing from 1 to 4 carbon atoms, preferably groups selected from the group consisting of methyl, ethyl, propyl, hydroxy substituted ethyl or propyl and mixtures thereof, preferably methyl, each $R^3$ is selected from the group consisting of hydrogen and hydroxy groups and each n is a number from 1 to 4, preferably from 2 to 3, more preferably 3, with no more than one hydroxy group in any $(C(R^3)_2)$ moiety. The $R^1$ groups can be branched and/or unsaturated. The $R^2$ groups can also be connected to form ring structures. A surfactant of this type is a $C_{10}$–$C_{14}$ fatty acylamidopropylene-(hydroxypropylene)sulfobetaine that is available from the Sherex Company under the trade name "Varion CAS sulfobetaine"®.

Suitable nonionic surfactants to be used herein are fatty alcohol ethoxylates and/or propoxylates which are commercially available with a variety of fatty alcohol chain lengths and a variety of ethoxylation degrees. Indeed, the HLB values of such alkoxylated nonionic surfactants depend essentially on the chain length of the fatty alcohol, the nature of the alkoxylation and the degree of alkoxylation. Surfactant catalogues are available which list a number of surfactants, including nonionics, together with their respective HLB values.

Particularly suitable for use herein as nonionic surfactants are the hydrophobic nonionic surfactants having an HLB (hydrophilic-lipophilic balance) below 16 and more preferably below 15. Those hydrophobic nonionic surfactants have been found to provide good grease cutting properties.

Preferred nonionic surfactants for use herein are nonionic surfactants according to the formula RO—$(C_2H_4O)_n(C_3H_6O)_m$H, wherein R is a $C_6$ to $C_{22}$ alkyl chain or a $C_6$ to $C_{28}$ alkyl benzene chain, and wherein n+m is from 0 to 20 and n is from 0 to 15 and m is from 0 to 20, preferably n+m is from 1 to 15 and, n and m are from 0.5 to 15, more preferably n+m is from 1 to 10 and, n and m are from 0 to 10. The preferred R chains for use herein are the $C_8$ to $C_{22}$ alkyl chains. Accordingly, suitable hydrophobic nonionic surfactants for use herein are Dobanol R 91-2.5 (HLB=8.1; R is a mixture of $C_9$ and $C_{11}$ alkyl chains, n is 2.5 and m is 0), or Lutensol R TO3 (HLB=8; R is a C13 alkyl chains, n is 3 and m is 0), or Lutensol R AO3 (HLB=8; R is a mixture of $C_{13}$ and $C_{15}$ alkyl chains, n is 3 and m is 0), or Tergitol R 25L3 (HLB=7.7; R is in the range of $C_{12}$ to $C_{15}$ alkyl chain length, n is 3 and m is 0), or Dobanol R 23-3 (HLB=8.1; R is a mixture of $C_{12}$ and $C_{13}$ alkyl chains, n is 3 and m is 0), or Dobanol R 23-2 (HLB=6.2; R is a mixture of $C_{12}$ and $C_{13}$ alkyl chains, n is 2 and m is 0), or Dobanol R 45-7 (HLB=11.6; R is a mixture of $C_{14}$ and $C_{15}$ alkyl chains, n is 7 and m is 0) Dobanol R 23-6.5 (HLB=11.9; R is a mixture of $C_{12}$ and $C_{13}$ alkyl chains, n is 6.5 and m is 0), or Dobanol R 25-7 (HLB=12; R is a mixture of $C_{12}$ and $C_{15}$ alkyl chains, n is 7 and m is 0), or Dobanol R 91-5 (HLB=11.6; R is a mixture of $C_9$ and $C_{11}$ alkyl chains, n is 5 and m is 0), or Dobanol R 91-6 (HLB=12.5; R is a mixture of $C_9$ and $C_{11}$ alkyl chains, n is 6 and m is 0), or Dobanol R 91-8 (HLB=13.7; R is a mixture of $C_9$ and $C_{11}$ alkyl chains, n is 8 and m is 0), Dobanol R 91-10 (HLB=14.2; R is a mixture of $C_9$ to $C_{11}$ alkyl chains, n is 10 and m is 0), or mixtures thereof. Preferred herein are Dobanol R 91-2.5, or Lutensol R TO3, or Lutensol R AO3, or Tergitol R 25L3, or Dobanol R 23-3, or Dobanol R 23-2, or Dobanol R 23-10, or mixtures thereof. Dobanol R surfactants are commercially available from SHELL. Lutensol R surfactants are commercially available from BASF and the Tergitol R surfactants are commercially available from UNION CARBIDE.

Suitable anionic surfactants to be used herein include water soluble salts or acids of the formula $ROSO_3M$ wherein R is preferably a $C_6$–$C_{24}$ hydrocarbyl, preferably an alkyl or hydroxyalkyl having a $C_8$–$C_{20}$ alkyl component, more preferably a $C_8$–$C_{18}$ alkyl or hydroxyalkyl, and M is H or a cation, e.g., an alkali metal cation (e.g., sodium, potassium, lithium), or ammonium or substituted ammonium (e.g., methyl-, dimethyl-, and trimethyl ammonium cations and quaternary ammonium cations, such as tetramethyl-ammonium and dimethyl piperdinium cations and quaternary ammonium cations derived from alkylamines such as ethylamine, diethylamine, triethylamine, and mixtures thereof, and the like).

Other suitable anionic surfactants to be used herein include alkyl-diphenyl-ether-sulphonates and alkyl-carboxylates. Other anionic surfactants can include salts (including, for example, sodium, potassium, ammonium, and substituted ammonium salts such as mono-, di- and triethanolamine salts) of soap, $C_9$–$C_{20}$ linear alkylbenzenesulfonates, $C_8$–$C_{22}$ primary or secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl ester sulfonates such as $C_{14-16}$ methyl ester sulfonates; acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinate (especially saturated and unsaturated $C_{12}$–$C_{18}$ monoesters) diesters of sulfosuccinate (especially saturated and unsaturated $C_6$–$C_{14}$ diesters), acyl sarcosinates, sulfates of alkylpolysaccharides such as the sulfates of alkylpolyglucoside (the nonionic nonsulfated compounds being described below), branched primary alkyl sulfates, alkyl polyethoxy carboxylates such as those of the formula $RO(CH_2CH_2O)_kCH_2COO$—M+ wherein R is a $C_8$–$C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil. Further examples are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23 (herein incorporated by reference).

Preferred anionic surfactants for use herein are the alkyl benzene sulfonates, alkyl sulfates, alkyl alkoxylated sulfates, paraffin sulfonates and mixtures thereof.

The internal disinfecting polar phase according to the present invention has a pH of from 1 to 12, preferably from 3 to 10, and more preferably from 3 to 9. The pH can be adjusted by using alkalinizing agents or acidifying agents. Examples of alkalinizing agents are alkali metal hydroxides, such as potassium and/or sodium hydroxide, or alkali metal oxides such as sodium and/or potassium oxide. Examples of acidifying agents are organic or inorganic acids such as citric or sulfuric acid.

Solvents may be present in the internal disinfecting polar phase according to the present invention. These solvents will, advantageously, give an enhanced cleaning to the disinfecting wipes of the present invention. Suitable solvents for incorporation herein include propylene glycol derivatives such as n-butoxypropanol or n-butoxypropoxypropanol, water-soluble CARBITOL® solvents or water-soluble CELLOSOLVE® solvents. Water-soluble CARBITOL® solvents are compounds of the 2-(2-alkoxyethoxy)ethanol class wherein the alkoxy group is derived from ethyl, propyl or butyl. A preferred water-soluble carbitol is 2-(2-butoxyethoxy)ethanol also known as butyl carbitol. Water-soluble CELLOSOLVE® solvents are compounds of the 2-alkoxyethoxyethanol class, with 2-butoxyethoxyethanol being preferred. Other suitable solvents are benzyl alcohol, methanol, ethanol, isopropyl alcohol and diols such as 2-ethyl-1,3-hexanediol and 2,2,4-trimethyl-1,3-pentanediol and mixture thereof. Preferred solvents for use herein are n-butoxypropoxypropanol, butyl carbitol® and mixtures thereof. A most preferred solvent for use herein is butyl carbitol®.

The internal disinfecting polar phase herein may further comprise other optional ingredients including radical scavengers, chelating agents, thickeners, builders, buffers, stabilizers, bleach activators, soil suspenders, dye transfer agents, brighteners, anti dusting agents, enzymes, dispersant, dye transfer inhibitors, pigments, perfumes, and dyes and the like.

Suitable radical scavengers for use herein include the well-known substituted mono and di hydroxy benzenes and derivatives thereof, alkyl- and aryl carboxylates and mixtures thereof. Preferred radical scavengers for use herein include di-tert-butyl hydroxy toluene (BHT), p-hydroxy-toluene, hydroquinone (HQ), di-tert-butyl hydroquinone (DTBHQ), mono-tert-butyl hydroquinone (MTBHQ), tert-butyl-hydroxy anysole, p-hydroxy-anysol, benzoic acid, 2,5-dihydroxy benzoic acid, 2,5-dihydroxyterephtalic acid, toluic acid, catechol, t-butyl catechol, 4-allyl-catechol, 4-acetyl catechol, 2-methoxy-phenol, 2-ethoxy-phenol, 2-methoxy-4-(2-propenyl)phenol, 3,4-dihydroxy benzaldehyde, 2,3-dihydroxy benzaldehyde, benzylamine, 1,1,3-tris(2-methyl-4-hydroxy-5-t-butylphenyl) butane, tert-butyl-hydroxy-anyline, p-hydroxy anyline as well as n-propyl-gallate. Highly preferred for use herein is di-tert-butyl hydroxy toluene, which is for example commercially available from SHELL under the trade name IONOL CP®.

Typically, the radical scavenger, or a mixture thereof, is present in the internal water phase up to a level of 5% by weight, preferably from 0.001% to 3% by weight, and more preferably from 0.001% to 1.5%.

Suitable chelating agents to be used herein may be any chelating agent known to those skilled in the art such as the ones selected from the group consisting of phosphonate chelating agents, amino carboxylate chelating agents or other carboxylate chelating agents, or polyfunctionally-substituted aromatic chelating agents and mixtures thereof.

Such phosphonate chelating agents may include etidronic acid (1-hydroxyethylidene-bisphosphonic acid or HEDP) as well as amino phosphonate compounds, including amino alkylene poly (alkylene phosphonate), alkali metal ethane 1-hydroxy diphosphonates, nitrilo trimethylene phosphonates, ethylene diamine tetra methylene phosphonates, and diethylene triamine penta methylene phosphonates. The phosphonate compounds may be present either in their acid form or as salts of different cations on some or all of their acid functionalities. Preferred phosphonate chelating agents to be used herein are diethylene triamine penta methylene phosphonates. Such phosphonate chelating agents are commercially available from Monsanto under the trade name DEQUEST®.

Polyfunctionally-substituted aromatic chelating agents may also be useful herein. See U.S. Pat. No. 3,812,044, issued May 21, 1974, to Connor et al. Preferred compounds of this type in acid form are dihydroxydisulfobenzenes such as 1,2-dihydroxy -3,5-disulfobenzene.

A preferred biodegradable chelating agent for use herein is ethylene diamine N,N'-disuccinic acid, or alkali metal, or alkaline earth, ammonium or substitutes ammonium salts thereof or mixtures thereof. Ethylenediamine N,N'-disuccinic acids, especially the (S,S) isomer have been extensively described in U.S. Pat. No. 4,704,233, Nov. 3, 1987 to Hartman and Perkins. Ethylenediamine N,N'-disuccinic acid is, for instance, commercially available under the tradename ssEDDS® from Palmer Research Laboratories.

Suitable amino carboxylate chelating agents useful herein include ethylene diamine tetra acetate, diethylene triamine pentaacetate, diethylene triamine pentaacetate (DTPA), N-hydroxyethylethylenediamine triacetate, nitrilotri-acetate, ethylenediamine tetraproprionate, triethylenetetraaminehexa-acetate, ethanoldiglycine, propylene diamine tetracetic acid (PDTA) and methyl glycine di-acetic acid (MGDA), both in their acid form, or in their alkali metal, ammonium, and substituted ammonium salt forms. Particularly suitable to be used herein are diethylene triamine penta acetic acid (DTPA), propylene diamine tetracetic acid (PDTA) which is, for instance, commercially available from BASF under the trade name Trilon FS® and methyl glycine di-acetic acid (MGDA).

Further carboxylate chelating agents to be used herein includes malonic acid, salicylic acid, glycine, aspartic acid, glutamic acid, dipicolinic acid and derivatives thereof, or mixtures thereof.

Typically, the chelating agent, or a mixture thereof, is present in the internal polar phase at a level of from 0.001% to 5% by weight, preferably from 0.001% to 3% by weight and more preferably from 0.001% to 1.5%.

The disinfecting wipes according to the present invention are suitable for disinfecting various surfaces including animate surfaces (e.g. human skin) as well as inanimate surfaces including any hard-surfaces.

Regardless of its composition, the internal polar phase will comprise from about 38 to about 97% of the emulsion. Preferably, the internal polar phase will comprise from about 67 to about 96% of the emulsion. More preferably, the internal polar phase will comprise from about 75 to about 95% and most preferably from about 82 to about 94%, of the emulsion.

Where the internal polar phase comprises water as a major component, the internal phase can comprise water-soluble or dispersible materials that do not adversely affect the stability of the high internal phase inverse emulsion. One such material that is typically included in the internal water phase is a water-soluble electrolyte. The dissolved electrolyte minimizes the tendency of materials present in the lipid phase to also dissolve in the water phase. Any electrolyte capable of imparting ionic strength to the water phase can be used. Suitable electrolytes include the water soluble mono-, di-, or trivalent inorganic salts such as the water-soluble halides, e.g., chlorides, nitrates and sulfates of alkali metals and alkaline earth metals. Examples of such electrolytes include sodium chloride, calcium chloride, sodium sulfate, magnesium sulfate, and sodium bicarbonate. The electrolyte will typically be included in a concentration in the range of from about 1to about 20% of the internal water phase.

Other water-soluble or dispersible materials that can be present in the internal polar phase include thickeners and viscosity modifiers. Suitable thickeners and viscosity modifiers include polyacrylic and hydrophobically modified polyacrylic resins such as Carbopol and Pemulen, starches such as corn starch, potato starch, tapioca, gums such as guar gum, gum arabic, cellulose ethers such as hydroxypropyl cellulose, hydroxyethyl cellulose, carboxymethyl cellulose, and the like. These thickeners and viscosity modifiers will typically be included in a concentration in the range of from about 0.05 to about 0.5% of the internal phase.

Again, where water is a major constituent of the internal polar phase, water-soluble or dispersible materials that can be present in the internal phase include polycationic polymers to provide steric stabilization at the polar phase-lipid phase interface and nonionic polymers that also stabilize the emulsion. Suitable polycationic polymers include Reten 201, Kymene® 557H and Acco 711. Suitable nonionic polymers include polyethylene glycols (PEG) such as Carbowax. These polycationic and nonionic polymers will typically be included in a concentration in the range of from about 0.1 to about 1.0% of the polar phase.

3. Emulsifier

Another key component of the high internal phase inverse emulsion of the present invention is an emulsifier. In the emulsions of the present invention, the emulsifier is included in an effective amount. What constitutes an "effective amount" will depend on a number of factors including the respective amounts of the lipid and internal polar phase components, the type of emulsifier used, the level of impurities present in the emulsifier, and like factors. Typically, the emulsifier comprises from about I to about 10% of the emulsion. Preferably, this emulsifier will comprise from about I to about 6% of the emulsion. Most preferably, this emulsifier will comprise from about 1.5 to about 3% of the emulsion. While the singular "emulsifier" is used to describe this component, more than one emulsifier may be used when forming the emulsion. Indeed, as discussed below, it may be desirable to utilize both a primary and a secondary emulsifier when certain materials are employed. Though not intended to limit the scope of the invention, where two emulsifiers are utilized, preferred is where the primary emulsifier comprises from about 1 to about 8%, more preferably from about 1 to about 3%, most preferably from about 1.5 to about 2.5%, by weight of the emulsion; and the secondary emulsifier comprises from about 0.1 to about 2%, more preferably from about 0.1 to about 1.5%, most preferably from about 0.1 to about 1%, by weight of the emulsion.

With regard to emulsions which release significant levels of fluid under compressive and shear forces, Applicants have found that an important property of the emulsifier is that they have a melting point that at least as great as the ambient temperatures where the article will be used (e.g., 25° C.). Emulsifiers suitable for use in the present invention have melting points typically of at least about 35° C. Without wishing to be bound by theory, Applicants believe that when the emulsifier, which is at the interface of the nonpolar external phase and the internal polar phase, is a solid at ambient temperatures, emulsion breakage is facilitated when exposed to in-use pressures. In contrast, when the emulsifier is a liquid at ambient temperatures, it tends to flow under pressure, but does not break. Thus, more internal phase is held by the emulsion because breakage is less pronounced. The emulsifier also needs to be substantially soluble in nonpolar materials (e.g., lipids) or miscible with the nonpolar phase materials, especially at the temperatures at which the nonpolar material melts. It also should have a relatively low HLB value. Emulsifiers suitable for use in the present invention have HLB values typically in the range of from about 2 to about 5 and can include mixtures of different emulsifiers. Preferably, these emulsifiers will have HLB values in the range of from about 2.5 to about 3.5.

Any emulsifier having a melting point greater than the ambient temperature where the article of the present invention will be used may be employed to provide emulsions having the IPPR values that represent one aspect of the present invention. Representative emulsifiers (or mixtures of emulsifiers) having such melting points include sorbitan monostearate (e.g, Span 60), sorbitan tristearate (e.g., Span 65), and glyceryl monostearate. Other emulsifiers having such melting points include alkyl grafted silicone copolyols having $C_{16}$ and higher alkyl groups. Such grafted silicone copolyols (also referred to herein as organopolysiloxane-polyoxyalkylenes) have the following general formula:

4,698,178 (Huttinger et al.), issued Oct. 6, 1987 and U.S. Pat. No. 5,162,378 (Guthauser), issued Nov. 10, 1992 (herein incorporated by reference) that disclose uncrosslinked (i.e., c is 0) versions of these organopolysiloxane-polyoxyalkylene emulsifiers, and U.S. Pat. No. 4,853,474 (Bahr et al.), issued Aug. 1, 1989 and U.S. Pat. No. 5,136,068 (Bahr et al.), issued Aug. 4, 1992 (herein incorporated by reference) that disclose crosslinked (i.e., c is 1 or more) versions of these organopolysiloxane-polyoxyalkylene emulsifiers.

The aliphatic radicals represented by $R^2$ can include any of the $C_{16}$ to $C_{35}$, preferably $C_{18}$ to $C_{25}$ alkyl, and acetylenic hydrocarbons with paraffinic hydrocarbons being preferred such as, for example, ethyl, propyl, hexyl, decyl, dodecyl, octadecyl, and eicosyl.

The organic groups represented by $R^4$ can include for example $C_1$ to $C_{10}$ alkylene radicals such as methylene, dimethylene, trimethylene, pentamethylene and decamethylene; cycloalkylene radicals such as cyclohexylene; divalent aromatic radicals such as p-phenylene or o-phenylene; and oxygen containing radicals such as

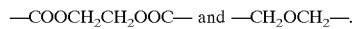

The terminal group represented by $R^5$ can include acyl radicals of $C_1$ to $C_{20}$, for example, acetyl, propionyl, butyryl, isobutyryl, lauroyl, myristoyl, and stearoyl, 3-carboxypentadecanoyl; alkyl radicals of $C_1$ to $C_{10}$ such as methyl, ethyl, propyl, butyl, and decyl; and hydrogen. Other

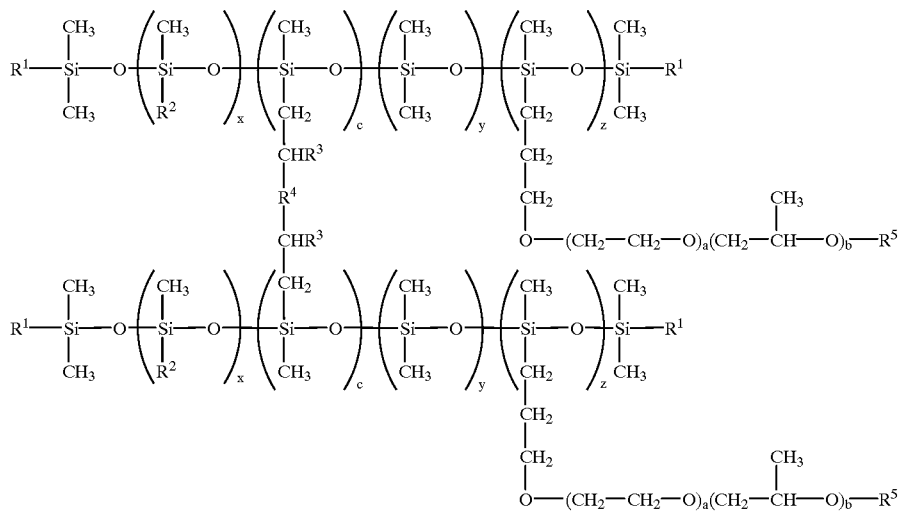

where $R^1$ is an aliphatic radical having from 1 to 25 carbon atoms which can be different for each different location; $R^2$ is an aliphatic radical having from 16 to 35 carbon atoms; $R^3$ is independently selected from hydrogen and aliphatic radicals having 1 to 3 carbon atoms which can be different for each different location; $R^4$ is an organic or organosiloxane group which contains no hydrolyzable bonds, is not adversely reactive with the ingredients the emulsifier is to stabilize and does not interfere with the formation of the organopolysiloxane-polyoxyalkylene; $R^5$ is a terminal group which is not adversely reactive with the ingredients the emulsifier is to stabilize and does not interfere with the formation of the organopolysiloxane-polyoxyalkylene; x is 1 to 100; y is 0 to 600; z is 1 to 100; x+y+z is at least 30; a is 4 to 40; b is 0 to 40; c is 0 to 5; and the ratio of a:b is from 20:80 to 100:0. See, for example, U.S. Pat. No.

terminating groups possessing substantially the same properties as the above illustrative examples and which are prepared in a similar manner and which function in an equivalent manner can also be used.

The aliphatic radical represented by $R^1$ can include any of the radicals illustrated above for $R^2$, but also includes the methyl radical.

The unit of the cross linking radical represented by $R^4$ can include hydrogen and monovalent $C_1$ to $C_3$ aliphatic radicals such as methyl, ethyl and propyl.

When c is 0, the organopolysiloxane-polyoxyalkylene emulsifier will be uncrosslinked. For crosslinked versions (i.e., c is 1 or more) of the organopolysiloxane-polyoxyalkylene emulsifier, it is preferred that the crosslinking bonds to $R^4$ not be hydrolyzable, and that $R^4$ contain no hydrolyzable bonds. In conventional organosiloxanepolyoxyalkylenes, some crosslinking can accidentally occur where the polyoxyalkylene is hydroxy terminated at one end. The hydroxy group can react with a silicon hydride creating a polyoxyalkylene bridge between two silicon backbone molecules. However, the degree to which this crosslinking can occur in the reaction process is not reliably predictable. Further, the SiOC bond formed at the hydroxy end of the bridge is subject to hydrolysis, especially under the extreme operating conditions described above.

By contrast, the preferred bridge bond of the organopolysiloxane-polyoxyalkylene useful in the present invention is a saturated carbon-silicon bond which is not hydrolyzable and is highly stable. Further, the organic or organosiloxane body $R^4$ of the cross linking bridge is selected to be free of hydrolyzable bonds. It is also important that it be free of reactive sites which would react with ingredients incorporated into the emulsion. Further, $R^4$ should not interfere with formation of the organopolysiloxane-polyoxyalkylene in any way.

A preferred cross linking radical is a vinyl terminated organosiloxane. An organosiloxane bridge cooperates with the siloxane backbones which it bridges to create a siloxane network at the interface of internal polar phase and external lipid phase of the emulsion. This network is thought to be important in effecting the stabilizing properties and characteristic of these emulsifiers. The most preferred organosiloxane cross linking material is tetramethyldivinyldisiloxane of the following formula:

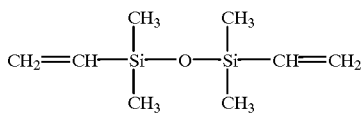

The organopolysiloxane-polyoxyalkylene molecules must themselves be soluble in nonpolar liquids. If the organopolysiloxane-polyoxyalkylene is readily dispersible in a nonpolar oil in a manner comparable to solubility, it is also considered "soluble" as that term is used herein. In order to effect such nonpolar oil solubility, the characteristics of the siloxane backbone can be muted either by the presence of aliphatic radicals appended to the siloxane backbone, or by the presence of a significant number of dimethyl siloxane groups in the siloxane chain, or both. The appended polyoxyalkylene groups (z) also enhance nonpolar oil solubility, though a quantity of either the dimethyl siloxane groups, the aliphatic groups or both are required in excess of the number of polyoxyalkylene groups included in the molecule. Hence, the number of siloxane groups (x) to which an aliphatic radical is appended is from 1 to 100. The number of dimethyl siloxane groups (y) is from 0 to 600. The number of polyoxyalkylene appended siloxane group is from 1 to 100. The combined total of those three different types of organo substituted siloxane groups (x+y+z) is at least 30, preferably at least 40.

The general formula above of the organopolysiloxane-polyoxyalkylene illustrates two organopolysiloxane-polyoxyalkylene molecules bridged by a single linking radical (i.e., where c is 1). However, where c is greater than 1, there can be more than one cross linking bridge between adjacent organopolysiloxane-polyoxyalkylene molecules, and/or there can be more than two organopolysiloxane-polyoxyalkylene molecules linked together, as shown by the formula in column 6 of U.S. Pat. No. 4,853,474, supra. The exact number of organopolysiloxane-polyoxyalkylene polymer molecules which will be bridged together will probably be not more than about 6. One limitation on such cross linking is that the overall molecular weight must not become so great as to cause the material to gel. The extent of crosslinking must thus also be regulated relative to the molecular weight of each individual organopolysiloxane-polyoxyalkylene polymer molecule being cross linked since the overall molecular weight must also be maintained sufficiently low to avoid gelling. A higher molecular weight in each individual polymer unit would require that there be less multiple cross linking between units.

For particularly preferred organopolysiloxane-polyoxyalkylene emulsifiers, $R^1$ is methyl; $R^2$ is $C_{18}$ to $C_{25}$ alkyl, $R^3$ is hydrogen; $R^4$ is —$(CH_3)_2$—Si—O—Si$(CH_3)_2$—; $R^5$ is hydrogen; x is 5 to 60; y is 0 to 150; z is 1 to 15; a is 10 to 30; b is 10 to 30; c is 0 to 1. Most preferred organopolysiloxane-polyoxyalkylene emulsifiers include those where $R^2$ is $C_{18}$ alkyl; x is 30 to 60; y is 0; z is 1 to 2; c is 0 to 1; the ratio of a:b is 50:50 to 100:0 or greater, such as stearyl dimethicone polyol (e.g., Dow Corning 2-5920) and stearyl dimethicone copolyol (e.g., Dow Corning 2-5733 and Dow Corning 2-5921), and those where $R^2$ is $C_{16}$ alkyl; x is 5 to 50; y is 25 to 150; z is 1 to 15; c is 0; the ratio of a:b is from 40:60 to 70:30, such as cetyl dimethicone copolyol (e.g., Goldschmidt Chemical's Abil EM 90).

4. Optional Emulsion Components

The high internal phase inverse emulsions of the present invention can also comprise other optional components typically present in moisture containing solutions of this type. These optional components can be present in either the continuous nonpolar phase or the internal polar phase and include perfumes, antimicrobial (e.g., antibacterial) actives, pharmaceutical actives, deodorants, opacifiers, astringents, skin moisturizers, and the like, as well as mixtures of these components. All of these materials are well known in the art as additives for such formulations and can be employed in effective, appropriate amounts in the emulsions of the present invention. A particularly preferred optional component that is included in the emulsions of wet-like cleansing articles according to the present invention is glycerin as a skin conditioning agent.

The emulsion component of the articles of the present invention is described and claimed herein in terms of components, and corresponding amounts of the components, that are present after emulsion formation. That is, when the stable emulsion is formed and applied to the carrier. It is understood that the description (components and amounts) of the emulsion also encompasses emulsions formed by combining the described components and levels, regardless of the chemical identity of the components after emulsification and application to the carrier.

C. Other Optional Article Components

Besides the high internal phase inverse emulsion, there are other optional components that can be included in the articles of the present invention, typically for the purpose of improving the cleaning performance of the article when the internal polar phase of the emulsion is released. Certain of these optional components cannot be present in the emulsion at significant levels (e.g., greater than 2% of the internal phase) because they can cause premature disruption of the emulsion. These include various anionic detergent surfactants that have relatively high HLB values (e.g., HLBs of from about 10 to about 25), such as sodium linear alkylbenzene sulfonates (LAS) or alkyl ethoxy sulfates (AES), as well as nonionic detergent surfactants such as alkyl ethoxylates, alkyl amine oxides, alkyl polyglycosides, zwitterionic detergent surfactants, ampholytic detergent surfactants, and cationic detergent surfactants such as cetyl trimethyl ammonium salts, and lauryl trimethyl ammonium salts. See U.S. Pat. No. 4,597,898 (Vander Meer), issued Jul. 1, 1986 (herein incorporated by reference), especially columns 12 through 16 for representative anionic, nonionic, zwitterionic, ampholytic and cationic detergent surfactants. Instead, these high HLB detergent surfactants can be applied or included in the article separately from the emulsion. For example, an aqueous solution of these high HLB detergent surfactants can be applied to the carrier either before or after application of the emulsion to the carrier. During wiping, the emulsion is disrupted, releasing the polar phase components so that they can then be combined with the high HLB detergent surfactant to provide improved hard surface cleaning.

Though the description of the invention generally relates to applying a single emulsion to the carrier, it is recognized that two or more different emulsions may be utilized in preparing a single article. In such embodiments, the emulsions may differ in a variety of ways, including but not limited to, the ratio of the internal polar phase and the external nonpolar phase, the emulsifiers used, the components used for either or both of the internal and external phases, and the like. Utilization of multiple emulsions in one article may be particularly desirable when two or more components are incompatible with each other, but can each be included in a separate emulsion. Alternatively, if a particular reaction is desired at the time of use, the reactants can be provided in separate emulsions. Upon shearing of the emulsions during use, the desired reaction will occur. For example, where foaming is desired during the wiping processes, a mild acid can be incorporated in the internal polar phase of one emulsion, while bicarbonate is incorporated in the internal polar phase of a second emulsion. Upon shearing of the emulsions during use, the reactants interact to provide the desired foam.

D. Preparation of Emulsion Treated Articles

In preparing the articles according to the present invention, the high internal phase emulsion is initially formulated. Typically, this is achieved by blending or melting together the nonpolar phase components and the emulsifier. The particular temperature to which this nonpolar/emulsifier mixture is heated will depend on the melting point of the external phase components. Typically, this mixture is heated to a temperature in the range from about 50° to about 90° C., preferably from about 70° to about 80° C., prior to being mixed, blended or otherwise combined with the internal polar phase components. The melted nonpolar/emulsifier mixture is then blended with the internal polar phase components and then mixed together, typically under low shear conditions to provide the emulsion.

Figure 3A:
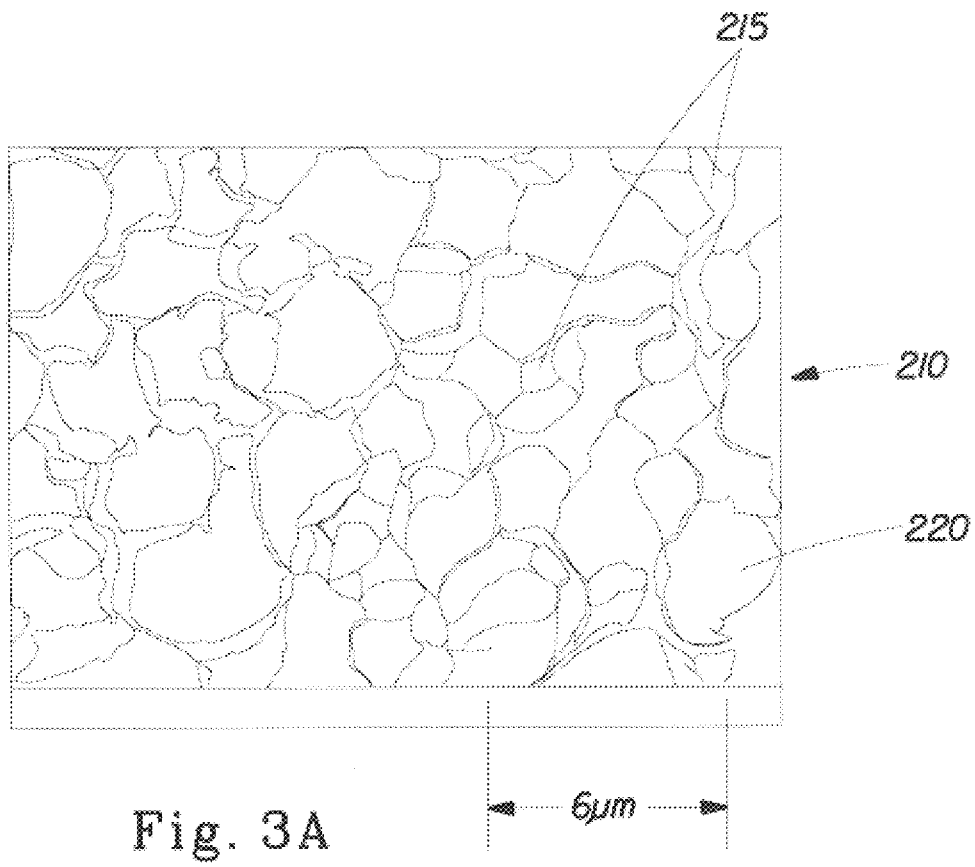
FIG. 3 is a photomicrograph of a high internal phase emulsion useful in the present articles. The emulsion was subjected to freeze-fracture and then photographed.
Figure 3:
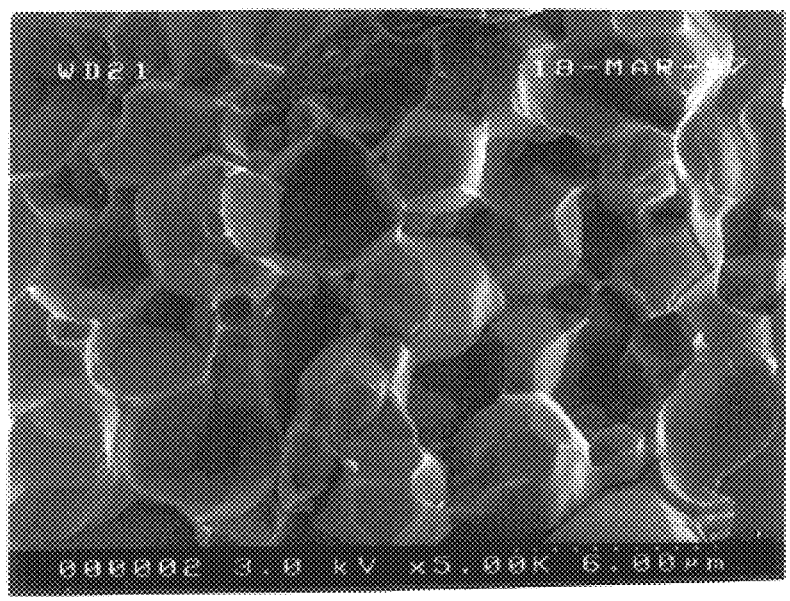
Figure 4A:
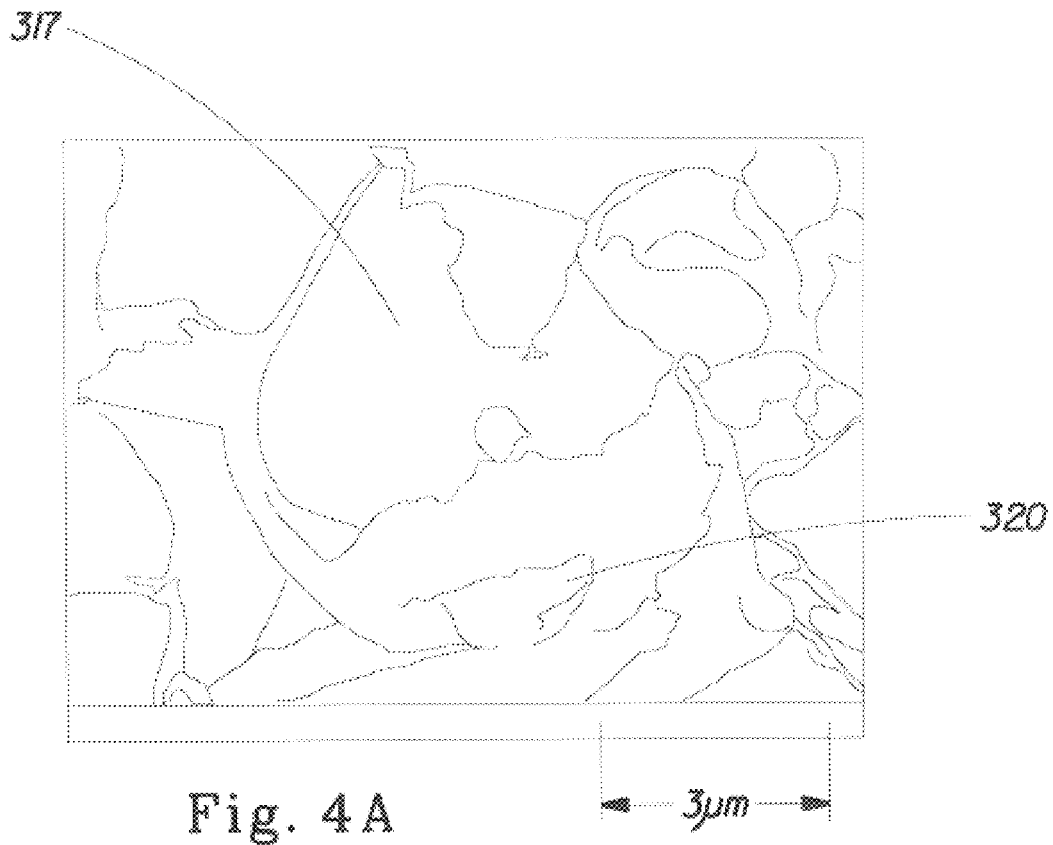
FIG. 4 is a photomicrograph of the emulsion shown in FIG. 3, but at a higher magnification.
Figure 4:
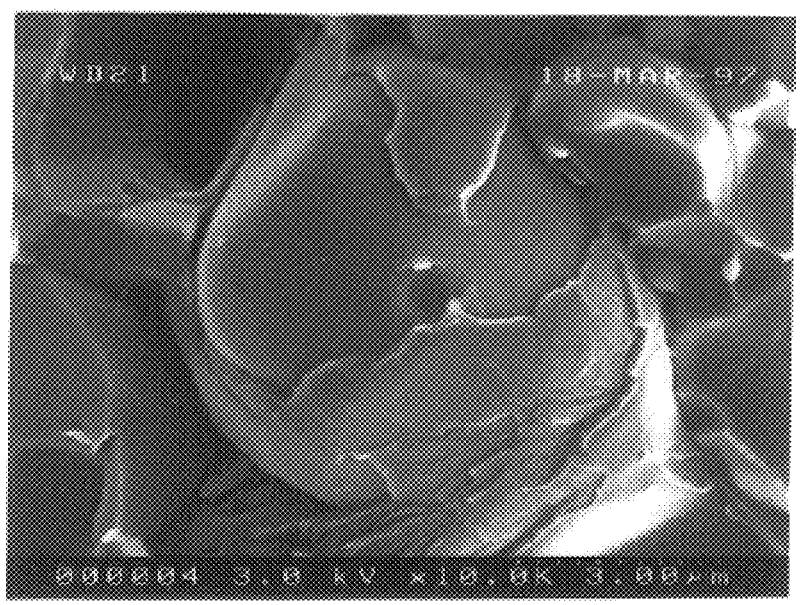
Figure 5A:
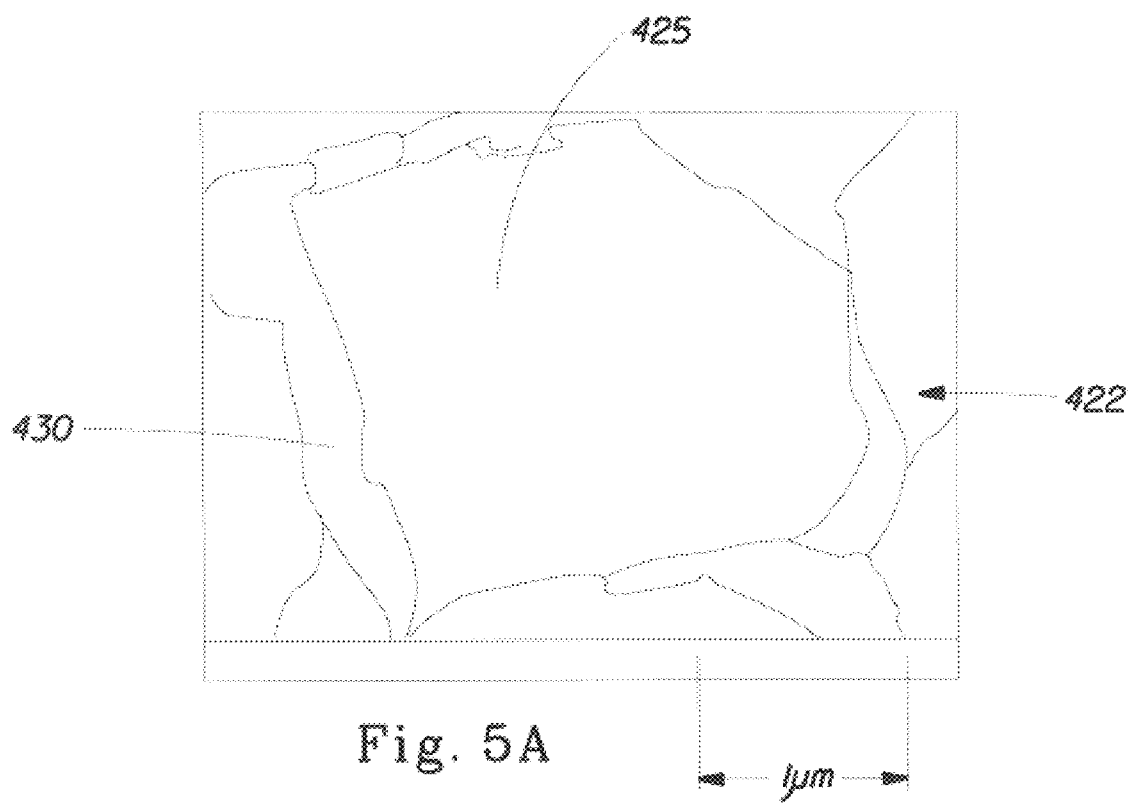
FIG. 5 is another photomicrograph of the emulsion shown in FIG. 4, but at a still higher magnification.
Figure 5:
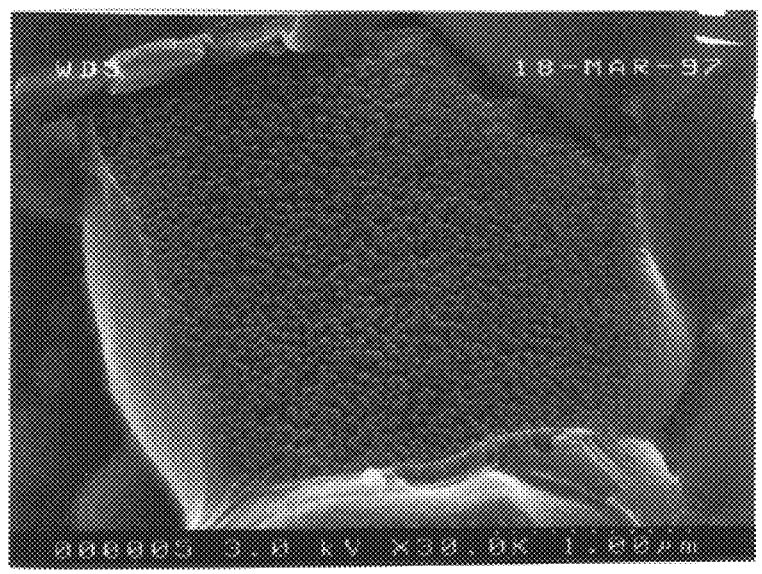

FIGS. 3 through 5 depict a representative emulsion useful in the present invention, at different magnifications. These figures are obtained by photographing a freeze-fractured emulsion. FIG. 3 shows the emulsion, depicted generally as 210, as comprising several distinct cells of external nonpolar phase and internal polar phase. A 6 μm length is shown for reference purposes. Numerous of the cells are intact (i.e., during the fracture process, the external nonpolar phase is not broken and the internal polar phase is retained by such cells), such as cells 215. Here, only the external phase can be seen. However, numerous of the cells were at the fracture interface and the external phase of these cells was broken and the internal polar phase was released. Such cells are depicted as 220.

Referring to FIG. 4, which is a further magnification of the emulsion of FIG. 3, it is observed that the external phase shown as 320 is lamellar in nature. 317 shows a smoother surface, but is still believed to be an inner layer of the external phase. A 3 μm length is shown as a reference point. FIG. 5 (a further magnification of FIG. 4) shows a close-up view of a cell, shown generally as 422, corresponding to a fractured cell shown as 220 in FIG. 3. Cell 422 clearly comprises an internal polar phase 425 and an external nonpolar phase 430. A 1 μm length is shown for references purposes. As the photograph of FIG. 5 is a freeze-fracture of the emulsion, very small ice crystals may be seen in the internal polar phase 422, which in this case comprises primarily water. Also, the external phase 430 has a thickness on the order of 0.2 μm or less.

This high internal phase inverse emulsion is then applied in a fluid or plastic state at the temperatures indicated above to a carrier. Any of a variety of methods that apply materials having a fluid or plastic consistency can be used to apply this emulsion. Suitable methods include spraying, printing (e.g., flexographic or screen printing), coating (e.g., gravure coating), extrusion, or combinations of these application techniques, e.g. spraying the detergent surfactant on the paper web, followed by gravure coating of the emulsion on the detergent treated web. A preferred method for application of the emulsion is via extrusion.

The emulsion can be applied either to one or both surfaces of the carrier, or it can be applied to the inner and/or outer surface(s) of two or more plies that make up the carrier. For example, in the case of a two ply carrier, the emulsion can be applied to the inner surface of one or both of the plies, leaving the outside surface of the carrier free of the emulsion. This carrier design minimizes transfer of wax and emulsifier to the surface being cleaned, which is especially desirable when higher loadings of emulsion are used to provide more liquid for cleaning. For example, to provide the level of liquid of a typical wipe for cleaning hard surfaces, a loading of emulsion of five times the weight of the carrier or greater might be used. The application of the emulsion to both sides of the carrier can be either sequential or simultaneous. Once the emulsion has been applied to the substrate, it is allowed to cool and solidify to form a solidified, typically discontinuous coating or film on the surface of the carrier. However, the emulsion can be applied to the carrier such that a continuous or discontinuous coating results.

The emulsion can be applied nonuniformly to the surface (s) of the carrier. By "nonuniform" is meant that the amount, pattern of distribution, etc. of the emulsion can vary over the surface(s) of the material being treated. For example, some portions of the surface of the carrier can have greater or lesser amounts of the emulsion, including portions of the surface that do not have any emulsion (i.e., application results in discontinuous emulsion coating). The high internal phase inverse emulsion can be applied to the carrier at any point after it has been dried. For example, the emulsion can be applied to the carrier after it has been creped from a Yankee dryer. Usually, it is preferred to apply the emulsion to the paper web as it is being unwound from a parent roll and prior to being wound up on smaller, finished product rolls.

FIG. 1 illustrates one method where the emulsion is sprayed onto a carrier 10. Referring to FIG. 1, this spray system has a spray head 12 that applies a dispersed spray 14 of the emulsion onto carrier 10.

This spray system is actuated by an assembly that consists of a ball screw drive 16 that is connected by coupling 18 to a piston 26 of hydraulic cylinder 22. A portion of cylinder 22 is shown in FIG. 1 as being filled with the high internal phase inverse emulsion as indicated by 30. Cylinder 22 is heated to keep emulsion 30 in a fluid or plastic state. Emulsion 30 enters cylinder 22 via a 4-way coupling 34 that has a line 38 connected to a heated filling port 42. Coupling 34 also has a line 46 that is connected to pressure gauge 50 and spray head 12. There are three valves indicated as 56, 58 and 60 that control the flow of the emulsion in lines 38 and 46. The spray system shown in FIG. 1 also has a line 64 connected to spray head 12 that allows air indicated generally as 68 to be admitted to the spray head. Line 64 also has a pressure gauge and regulator 72 for controlling and measuring the air pressure in line. Lines 64 and 46 are heated to maintain the emulsion in a molten state prior to application to the carrier.

To fill cylinder 22 with emulsion 30, valves 56 and 60 are closed and valve 58 is opened. Ball screw drive 16 is actuated so that piston 26 moves to the left. The vacuum created in cylinder 22 draws the emulsion from filling port 42 through line 38 and into cylinder 22. To provide emulsion from cylinder 22 to spray head 12, valve 58 is closed and valves 56 and 60 are opened. The ball screw drive 16 is actuated so that piston 26 moves to the right. This forces emulsion 30 out of cylinder 22 and into line 46 of coupling 34. The emulsion then passes through valve 60 and into the spray head 12 where it is dispersed by incorporation of air from line 64 to provide dispersed spray 14 that is then applied to carrier 10.

Figure 2:
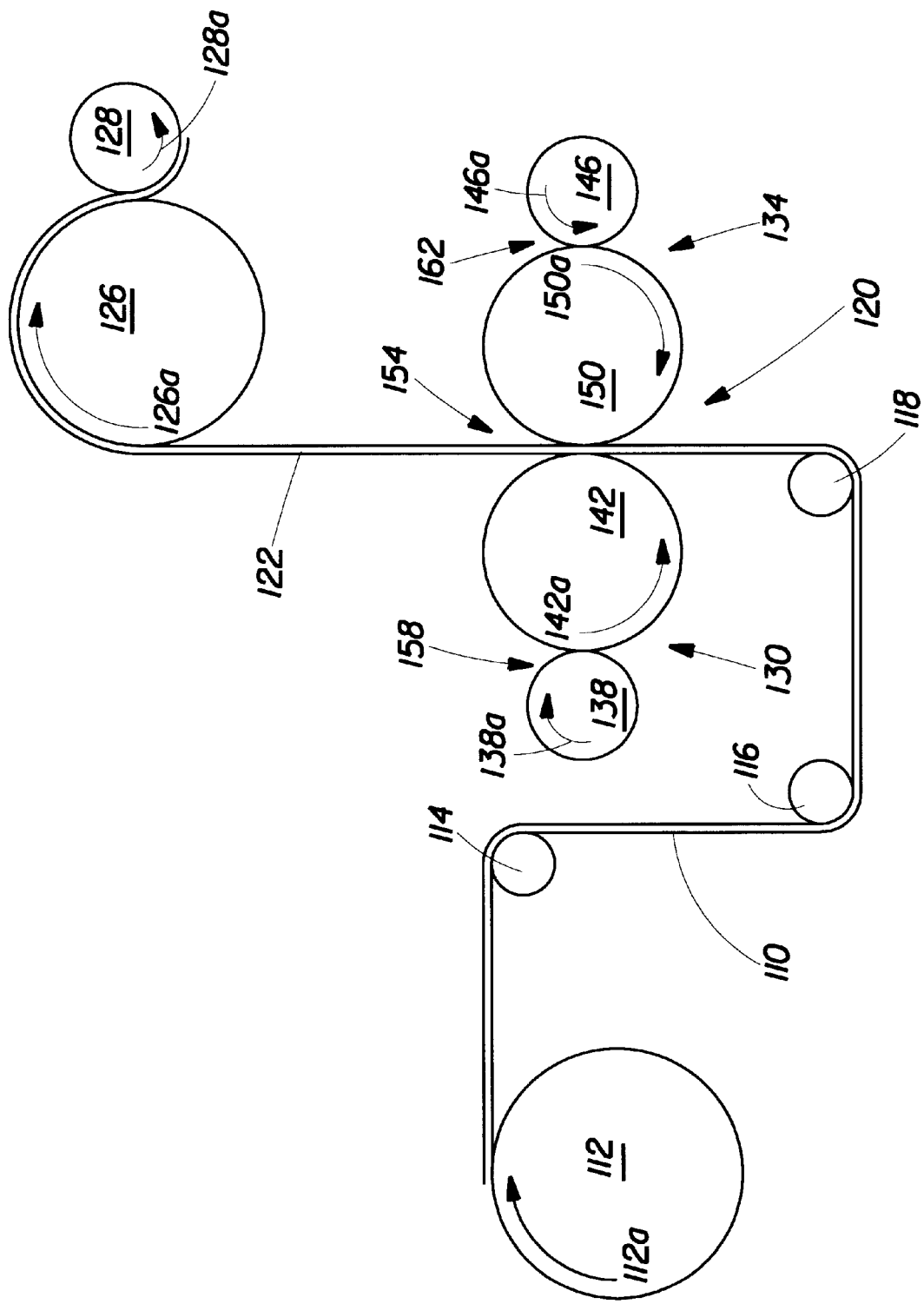
FIG. 2 is a schematic representation illustrating a system for applying the high internal phase inverse emulsions of the present invention by gravure coating to a carrier such as a treated paper web.

FIG. 2 illustrates an alternative method for applying the high internal phase inverse emulsion involving a flexible rotogravure coating system. Referring to FIG. 2, a carrier 110 is unwound from parent tissue roll 112 (rotating in the direction indicated by arrow 112a) and advanced around turning rolls 114, 116 and 118. From turning roll 118, carrier 110 is advanced to a gravure coating station indicated generally as 125 where the emulsion is then applied to both sides of the carrier. After leaving station 125, carrier 110 becomes a treated web indicated by 122. Treated web 122 is advanced to surface rewinder roll 126 (rotating in the direction indicated by arrow 126a) and then wound up on finished product roll 128 (rotating in the direction indicated by arrow 128a). Station 125 comprises a pair of heated linked gravure presses 130 and 134. Press 130 consists of a smaller anilox cylinder 138 and a larger print plate cylinder 142; press 134 similarly consists of a smaller anilox cylinder 146 and a larger print plate cylinder 150. Anilox cylinders 138 and 146 each have a ceramic or chrome surface, while print plate cylinders 142 and 150 each have a relief patterned rubber, urethane, or photopolymer surface. These anilox and print plate cylinders rotate in the directions indicated by arrows 138a, 142a, 146a and 150a, respectively. As shown in FIG. 2, print plate cylinders 142 and 150 are opposed to one another and provide a nip area indicated by 154 through which carrier 110 passes.

Hot, molten (e.g., 60° C.) emulsion is pumped to or sprayed onto each of these linked gravure presses 130 and 134 at the nip areas indicated by arrows 158 and 162, respectively, at a constant volumetric flow rate. (Emulsion delivered to presses 130 and 134 may be the same or different.) In other words, the emulsion is added to the linked gravure presses 130 and 134 at the same rate as the emulsion is being applied to the carrier 110. This eliminates emulsion "build-up" in the system. As anilox cylinders 138 and 146 rotate in the directions indicated by arrows 138a and 146a, they act as rotating doctor blades to spread the emulsion evenly across the surfaces of print plate cylinders 142 and 150, respectively, and to remove excess emulsion from the print plates of cylinders 142 and 150.

The emulsion that is spread onto print plate cylinders 142 and 150 (rotating in the opposite direction as indicated by arrows 142a and 150b) is then transferred to both sides of carrier 110 at nip area 154. The amount of the emulsion transferred to carrier 110 can be controlled by: (1) adjusting the width of nip area 154 between print plate cylinders 142 and 150; (2) adjusting the width of nip areas 158 and 162 between anilox/print plate cylinder pairs 138/142 and 146/150; (3) the print image relief (i.e., valley depth) of the print plate on cylinders 142 and 150; (4) the print area (i.e., valley area) of the print plate on cylinders 142 and 150; and/or (5) the print pattern of the print plate on cylinders 142 and 150.

E. Test Methods

1. Internal Polar Phase Loss After 28 Days

The following is a description of how retention properties of articles of the present invention are monitored and measured after storage at 125° F. for 6 days in a moisture impermeable container.

A test article is placed in a tared moisture impermeable container and the weight of the container with the article and the cap is measured. As used herein, "moisture impermeable" means that less than 10 mg of weight loss of the unopened container results under these conditions. The container is sealed and placed in a 125° F. oven for 6 days. (Sealing is confirmed by a weight loss of less than 10 milligrams after the container is removed from the oven.) The cap is removed and the weight of the container and article is taken as the day zero weight. The opened container and article is then placed in a 72° F., 50% relative humidity environment. The container and article weight is measured periodically (e.g., once a day) for 28 days. At the end of the 28 day period, the container and article are placed in a 212° F. oven for 24 hours. The weight of the container and article is then measured and this weight is recorded as the base weight of the container and article. The loss of internal phase is then calculated according to the following formulas;

Total internal phase weight=day zero weight−base weight

Internal Phase Loss at day (x)=(day zero weight−day (x) weight)

Percent Internal Phase loss=Internal Phase Loss/total internal phase weight*100%

The $IPPL_{28}$ value is the Percent Internal Phase loss at 28 days.

2. Internal Polar Phase Release

To study the amount of fluid released from the internal polar phase under pressure, the following steps are performed on test articles.

1. A tared test article is placed on a solid flat plexiglass® sheet.
2. A solid steel pipe 8 in. long and 2½ in. in diameter weighing 5130 grams, providing 1.4 PLI (pounds per linear inch) of force, is rolled over the test article, releasing a portion of the internal polar phase of the emulsion.
3. The test article is placed in a 50° C. oven for 60 minutes to evaporate internal polar phase released from the emulsion.
4. The test article is removed from the oven and weighed to obtain the compressed article weight.
5. The test article is placed in a 212° F. oven for 24 hours. The weight of the test article is then measured and this weight is recorded as the base weight of the article.
6. Steps 1 through 5 are repeated five times in order to calculate an average and standard deviation of the measurements.

The Internal Polar Phase Release value for the test article is calculated according to the following formulas:

Total polar phase weight $_{(test)}$=tared article weight−base weight

Polar phase released $_{(test)}$=tared article weight−compressed article weight.

% Polar phase released $_{(test)}$=polar phase released/total polar phase weight *100

To correct for internal polar phase release due to evaporation from unbroken emulsion, the following steps are performed.

1. A tared control article is placed in a 50° C. oven for 60 minutes to evaporate internal polar phase released from the emulsion.
2. The control article is removed from the oven and weighed to obtain the correction article weight.
3. The control article is placed in a 212° F. oven for 24 hours. The weight of the article is then measured and this weight is recorded as the control base weight of the article.
4. Steps 1 through 4 are repeated five times in order to calculate an average and standard deviation of the measurements.

The control Internal Polar Phase Release value is calculated according to the following formulas:

Total polar phase weight $_{(control)}$=tared control article weight−base weight Polar phase released $_{(control)}$=tared control article weight−correction article weight.

% Polar phase released $_{(control)}$=polar phase released/total polar phase weight×100.

% Polar phase released $_{(corrected)}$=% Polar phase released $_{(test)}$−% Polar phase released $_{(control)}$ As used herein, the IPPR value of an article is the % Polar phase released $_{(corr.)}$ value.

F. Specific Illustrations and IPPL$_{28}$ and IPPR Properties of Wet-Like Cleaning Articles According to the Present Invention Comparative Example A and B Emulsion Preparation An emulsion is prepared from the following ingredients shown below:

| Ingredients | Amount (gm) | Percentage |
| --- | --- | --- |
| Yellow Ceresine Wax (Strahl & Pitsch SP983) | 40 grams | 4.00% |
| White Ozokerite Wax (Strahl & Pitsch SP1190) | 40 grams | 4.00% |
| Petrolatum | 10 grams | 1.00% |
| Dow Corning 2-5759-13140-112A | 20 grams | 2.00% |
| CP1215 (ICI america) | 5 grams | 0.5% |
| Aqueous Phase of: 97.5% distilled water 0.1% Na$_2$SO$_4$ 0.3% Glydant Plus 0.1% Na$_4$EDTA 2.0% Propylene Glycol | 885 grams | 88.5% |

In formulating the aqueous phase component, the four ingredients are added to the distilled water and then heated to 160° F. (71.1° C.). The remaining five lipid phase ingredients are heated, with mixing to a temperature of ~190° F. (87.7° C.) until melted. The polar internal phase and non-polar external phase components are then combined in a stainless steel vessel and mixed with a Hobart Model 100-C mixer on the low speed setting while allowing the ingredients to cool slowly. Mixing is continued until the emulsion forms. Emulsion formation is evidenced by an increase in viscosity above 2000 centipoise as measured with a Lab-Line Instruments rotating disc viscometer.

The substrate used in this Example was a 9.5 lb/3000 ft$^2$ paper substrate composed of 100% cellulose cut to 12 in.×12 in. The emulsions are extruded on to the surface of the substrate in continuous beads by using a heated 30 cc syringe and needle arrangement. The emulsion is suctioned into the syringe at 70° C. and the assembly is placed in a 70° C. oven for five minutes. Emulsion beads are extruded at ¼ in. intervals and applied over a six inch wide by eight inch long region. Six samples are prepared and allowed to cool at room temperature for at least one hour prior to performing the breaking test. This time is necessary to allow for full cooling of the emulsion components prior to breaking. The substrate was then folded to attain the three layer system with dimensions of 12 in.×6 in., weighed and placed on a sheet of plexiglass. The article's IPPR value is determined in accordance with the above procedure.

In addition to the emulsion formed above, a second comparative example (Comparative Example B) was performed using the same formula and procedure above. The only change to the formula is the use of Dow Corning 5200 in place of the Dow Corning 2-5759-13140-112A. The IPPR data for these two comparative examples are summarized in Table 1 below.

Representative Example 1

Emulsion Preparation

An emulsion is prepared from the following ingredients shown below:

| Ingredients | Amount (gm) | Percentage |
| --- | --- | --- |
| Yellow Ceresine Wax (Strahl & Pitsch SP983) | 40 grams | 4.00% |
| White Ozokerite Wax (Strahl & Pitsch SP1190) | 40 grams | 4.00% |
| Petrolatum | 10 grams | 1.00% |
| Dow Corning 2-5733-13542-96 | 20 grams | 2.00% |
| CP1215 (ICI America) | 5 grams | 0.5% |
| Aqueous Phase of: 97.5% distilled water 0.1% Na$_2$SO$_4$ 0.3% Glydant Plus 0.1% Na$_4$EDTA 2.0% Propylene Glycol | 885 grams | 88.5% |

The emulsion was formed in the way described in Comparative Example A. The substrate and article preparation are the same as described in Comparative Example A.

In addition to the emulsion formed above, a second representative example (Representative Example 2) was performed using the same formula and procedure above. The only change to the formula was the use of Dow Corning 2-5733-13542-100 in place of the Dow Corning 2-5733-13542-96.

The IPPR data for the comparative and representative examples is provided in Table 1.

TABLE 1

| Sample | A | B | 1 | 2 |
|---|---|---|---|---|
| Waxes | | | | |
| SP983 | 4.00% | 4.00% | 4.00% | 4.00% |
| SP1190 | 4.00% | 4.00% | 4.00% | 4.00% |
| Petrolatum | 1.00% | 1.00% | 1.00% | 1.00% |
| Emulsifiers | | | | |
| Dow Corning 5200 | | 2.00% | | |
| Dow Corning lot #112A | 2.00% | | | |
| Dow Corning 2-5733 lot #13542-96 | | | 2.00% | |
| Dow Corning 2-5733 lot #13542-100 | | | | 2.00% |
| CP1215 | 0.50% | 0.50% | 0.50% | 0.50% |
| Aqueous Phase Total | 88.50% | 88.50% | 88.50% | 88.50% |
| Aqueous Components | | | | |
| Distilled Water | 97.50% | 97.50% | 97.50% | 97.50% |
| Sodium Sulfate | 0.10% | 0.10% | 0.10% | 0.10% |
| 0.1% EDTA | 0.10% | 0.10% | 0.10% | 0.10% |
| 0.3% Glydant Plus | 0.30% | 0.30% | 0.30% | 0.30% |
| Propylene Glycol | 2.00% | 2.00% | 2.00% | 2.00% |
| Breaking Data | | | | |
| IPPR Value | 23.4% | 34.8% | 52.5% | 62.3% |
| Standard deviation | 6.6% | 5.8% | 3.8% | 16.7% |

The results of Table 1 indicate that the articles of the present invention release more fluid during in-use wiping. As can be seen from the comparison, the selection of different emulsifiers alone in Representative Examples 1 and 2 provided significantly improved polar phase release compared with Comparative Examples A and B. Thus, all other things being constant, the emulsion of the article delivers more liquid under typical use conditions.

Comparative Example C

The carrier used in this test was a 9.5 Lb/ 3000 ft$^2$ paper substrate composed of 100% cellulose cut to 12 in.×12 in.

A) Emulsion Preparation

An emulsion is prepared from the following ingredients shown in Table II below:

TABLE II

| Ingredients | Amount (gm) | Percentage |
|---|---|---|
| Yellow Ceresine Wax (Strahl & Pitsch SP983) | 18 | 6% |
| Petrolatum (Fisher) | 3 | 1% |
| Dow Corning 2-5759-13140-103A | 9 | 3% |
| Aqueous Phase 95% distilled water 5% propylene glycol | 270 | 90% |

The lipid phase ingredients (yellow ceresine wax, petrolatum, and Dow Corning 2-5759-13140-103A) are heated and stirred in a 500 ml stainless steel beaker to a temperature of 180° F. (82.8° C.) until melted. The internal polar phase component is prepared by adding 13.5 gm of Propylene Glycol and 256.5 gm of distilled water to a 500 ml glass beaker, followed by mixing. A portion (100 g) of this polar solution is added to the beaker containing the lipid phase component. The combined mixture is heated to 160° F. (71° C.) and then mixed with a "Lightnin' TS2510" mixer at 500 rpm while allowing the ingredients to cool until the emulsion forms. This formation is noted by a dramatic increase in viscosity above 2000 cPs as measured by a Brookfield rotational viscometer. At this point the remainder of the polar phase may be added with mixing. The temperature is adjusted to 160° F. (71° C.) and then allowed to cool while mixing until the remaining polar phase is incorporated into the emulsion. This will again be noticed by a dramatic increase in the viscosity of the mixture.

The emulsion is extruded on to the surface of the substrate in continuous beads using a Pam 600 hot melt adhesive delivery gun equipped with a nozzle of 0.7 mm diameter.

Representative Example 3

A representative emulsion useful in the present invention is prepared from the following ingredients shown below:

TABLE III

| Ingredients | Amount (gm) | Percentage |
|---|---|---|
| Yellow Ceresine Wax (Strahl & Pitsch SP983) | 9 | 3% |
| White ozokerite Wax (Strahl & Pitsch SP1190 | 9 | 3% |
| Petrolatum (Fisher) | 3 | 1% |
| Dow Corning 2-5759-13140-103A | 9 | 3% |
| Aqueous Phase 95% distilled water 5% propylene glycol | 270 | 90% |

The emulsion is formed in the same manner as described in Comparative Example C. The emulsion differ only in the composition of the wax phases. The emulsion was extruded on to the surface of the substrate in the same manner as described in Comparative Example C.

The IPPL results for Comparative Example C and Representative Example 3 are shown in Table 3.

TABLE 3

| Days | Comparative Example C IPPL | Representative Example 3 IPPL |
|---|---|---|
| 0 | 0.0 | 0.0 |
| 2 | 49.1 | 5.8 |
| 3 | 53.8 | 6.4 |
| 4 | 56.3 | 6.8 |
| 5 | 58.1 | 7.1 |
| 7 | 60.6 | 7.6 |
| 10 | 63.0 | 8.4 |
| 13 | 65.0 | 9.2 |
| 15 | 66.0 | 9.8 |
| 17 | 66.3 | 10.1 |
| 19 | 66.6 | 10.2 |
| 21 | 67.6 | 11.0 |
| 24 | 67.9 | 11.3 |
| 26 | 68.6 | 12.0 |
| 28 | 68.9 | 12.6 |

The IPPL$_{28}$ values of Comparative Example C and Representative Example 3 demonstrate the improved fluid retention properties of the articles of the present invention. In this regard, by modifying only the composition of the external nonpolar phase of the emulsion, significant benefits are seen in terms of internal polar phase retention by the article. All other things being equal, the representative article will retain much more fluid to be released during the wiping process.

What is claimed is:

1. A wet-like cleaning article comprising:
   a. a carrier; and
   b. an emulsion applied to the carrier, the emulsion comprising a continuous external lipid phase, wherein the external lipid phase comprises at least two lipids having different melt characteristics, and at least about 50% of the external lipid phase melts at or above 50° C.; and an internal polar phase dispersed in the external lipid phase; and an effective amount of an emulsifier capable of forming the emulsion when the external lipid phase is in a fluid state, wherein the emulsifier has a melting point of at least about 35° C.;

wherein the emulsion comprises at least 38%, by weight, internal polar phase and wherein the article has an $IPPL_{28}$ value of not more than about 60% and an IPPR value of at least about 30%.

2. The wet-like cleaning article of claim 1, wherein the article has an $IPPL_{28}$ value of not more than about 50%.

3. The wet-like cleaning article of claim 2, wherein the article has an $IPPL_{28}$ value of not more than about 40%.

4. The wet-like cleaning article of claim 3, wherein the article has an $IPPL_{28}$ value of not more than about 30%.

5. The wet-like cleaning article of claim 4, wherein the article has an $IPPL_{28}$ value of not more than about 20%.

6. The wet-like cleaning article of claim 5, wherein the article has an $IPPL_{28}$ value of not more than about 10%.

7. The wet-like cleaning article of claim 1, wherein the article has an $IPPL_{28}$ value of from about 10 to about 60%.

8. The wet-like cleaning article of claim 7, wherein the article has an $IPPL_{28}$ value of from about 10 to about 50%.

9. The wet-like article of claim 1 wherein the article has an IPPR value of at least about 50%.

10. The wet-like article of claim 9 wherein the article has an IPPR value of at least about 60%.

11. The wet-like article of claim 1 wherein the article has an IPPR value of at least about 40%.

12. The wet-like article of claim 11 wherein the article has an IPPR value of at least about 70%.

13. The wet-like article of claim 1 wherein the article has an IPPR value of from about 30 to about 90%.

14. The wet-like article of claim 13 wherein the article has an IPPR value of from about 40 to about 90%.

15. The wet-like article of claim 1 wherein the article has an $IPPL_{28}$ value of not more than about 50% and an IPPR value of at least about 40%.

16. The wet-like article of claim 15 wherein the article has an $IPPL_{28}$ value of not more than about 40% and an IPPR value of at least about 50%.

17. The wet-like article of claim 16 wherein the article has an $IPPL_{28}$ value of not more than about 30% and an IPPR value of at least about 60%.

18. The wet-like article of claim 17 wherein the article has an $IPPL_{28}$ value of not more than about 20% and an IPPR value of at least about 60%.

19. The wet-like article of claim 18 wherein the article has an $IPPL_{28}$ value of not more than about 10% and an IPPR value of at least about 60%.

20. The wet-like article of claim 19 wherein the article has an $IPPL_{28}$ value of not more than about 10% and an IPPR value of at least about 70%.

21. A wet-like cleaning article comprising:

a. a carrier; and b. an emulsion applied to the carrier, the emulsion comprising:

(1) from about 2 to about 60% of a continuous solidified external lipid phase comprising a first lipid material having a peak melting point of from about 30° C. to about 60° C. and a second lipid material having a peak melting point of from about 50° C. to about 90° C., wherein the second lipid material has a peak melting point that is at least 10° C. greater than the peak melting point of the first lipid material;

(2) from about 38 to about 97% of an internal polar phase dispersed in the external lipid phase; and (3) an effective amount of an emulsifier capable of forming the emulsion when the external lipid phase is in a fluid state, wherein the emulsifier has a melting point of at least about 35° C.;

wherein the article has an $IPPL_{28}$ value of not more than about 60% and an IPPR value of at least about 30%.

22. The article of claim 21 wherein the carrier is selected from the group consisting of woven materials, nonwoven materials, foams, sponges, battings, balls, puffs, and films.

23. The article of claim 22 wherein s aid carrier is a paper web.

24. The article of claim 21 wherein the peak melting point of the first lipid material is from about 50 to about 60° C. and the peak melting point of the second lipid material is from about 65 to about 85° C.

25. The article of claim 24 wherein the second lipid material has a peak melting point that is at least 15° C. greater than the peak melting point of the first lipid material.

26. The article of claim 21 wherein the external lipid phase has a peak melting point in the range of from about 40° to about 80° C.

27. The article of claim 26 wherein the external lipid phase has a peak melting point in the range of from about 60° to about 70° C.

28. A wet-like cleaning article comprising:

a. a carrier; and b. an emulsion applied to the carrier, the emulsion comprising:

(1) from about 2 to about 60% of a continuous solidified external lipid phase comprising a mixture of waxy lipid materials having different melt characteristics and having a peak melting point of about 30° C. or higher;

(2) from about 38 to about 97% of an internal polar phase dispersed in the external lipid phase; and (3) an effective amount of an emulsifier capable of forming the emulsion when the external lipid phase is in a fluid state, the emulsifier having a melting point of at least about 35° C.;

wherein the article has an $IPPL_{28}$ value of not more than about 60% and an IPPR value of at least about 30%.

29. The article of claim 28 wherein the carrier is selected from the group consisting of woven materials, nonwoven materials, foams, sponges, battings, balls, puffs, and films.

30. The article of claim 29 wherein said carrier is a paper web.

31. The article of claim 28 wherein the emulsion comprises from about 3 to about 30% of said external lipid phase and from about 67 to about 96% of said internal polar phase.

32. The article of claim 31 wherein the emulsion comprises from about 4 to about 15% of said external lipid phase and from about 75 to about 95% of said internal polar phase.

33. The article of claim 28 wherein the waxy lipid material has a peak melting point in the range of from about 40° to about 80° C.

34. The article of claim 33 wherein the waxy lipid material has a peak melting point in the range of from about 60° to about 70° C.

35. The article of claim 28 wherein the emulsifier is selected from the group consisting of sorbitan-containing emulsifiers, glycerol-containing emulsifiers, alkyl-grafted silicone copolyol emulsifiers, and mixtures thereof.

36. The article of claim 35 wherein the emulsifier is an alkyl-grafted silicone polyol of the following structure:

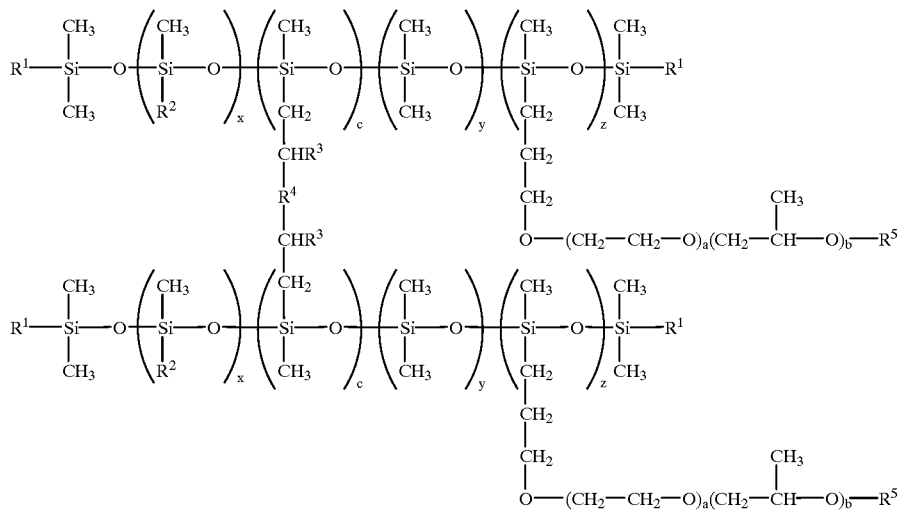

where $R^1$ is an aliphatic radical having from 1 to 25 carbon atoms which can be different for each different location; $R^2$ is an aliphatic radical having from 16 to 35 carbon atoms; $R^3$ is independently selected from hydrogen and aliphatic radicals having 1 to 3 carbon atoms which can be different for each different location; $R^4$ is an organic or organosiloxane group which contains no hydrolyzable bonds, is not adversely reactive with the ingredients the emulsifier is to stabilize and does not interfere with the formation of the organopolysiloxane-polyoxyalkylene; $R^5$ is a terminal group which is not adversely reactive with the ingredients the emulsifier is to stabilize and does not interfere with the formation of the organopolysiloxane-polyoxyalkylene; x is 1 to 100; y is 0 to 600; z is 1 to 100; x+y+z is at least 30; a is 4 to 40; b is 0 to 40; c is 0 to 5; and the ratio of a:b is from 20:80 to 100:0.

* * * * *